(12) United States Patent
Ferguson, Jr. et al.

(10) Patent No.: US 10,948,350 B2
(45) Date of Patent: Mar. 16, 2021

(54) SYSTEMS FOR DETECTING VASCULAR AND ARTERIAL DISEASE IN ASYMPTOMATIC PATIENTS AND RELATED METHODS

(71) Applicant: East Carolina University, Greenville, NC (US)

(72) Inventors: T. Bruce Ferguson, Jr., Raleigh, NC (US); Bryent Tucker, Rocky Mount, NC (US); Sunghan Kim, Winterville, NC (US); Cheng Chen, Greenville, NC (US); William Hempstead, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 16/560,335

(22) Filed: Sep. 4, 2019

(65) Prior Publication Data
US 2020/0072670 A1     Mar. 5, 2020

Related U.S. Application Data
(60) Provisional application No. 62/727,293, filed on Sep. 5, 2018.

(51) Int. Cl.
*G01J 3/28* (2006.01)
*G01J 3/32* (2006.01)
(Continued)

(52) U.S. Cl.
CPC .......... *G01J 3/2823* (2013.01); *A61B 5/0075* (2013.01); *A61B 5/1455* (2013.01); *G01J 3/2803* (2013.01);
(Continued)

(58) Field of Classification Search
CPC .......... G01J 3/2823; G01J 3/2803; G01J 3/32; G01J 3/36; G01J 2003/1213;
(Continued)

(56) References Cited

U.S. PATENT DOCUMENTS

| 8,644,911 B1 | 2/2014 | Panasyuk |
| 9,226,673 B2 | 1/2016 | Ferguson, Jr. et al. |

(Continued)

FOREIGN PATENT DOCUMENTS

WO    WO 2016/153741 A1    9/2016

OTHER PUBLICATIONS

Tian et al., "Quantitative characterization of turbidity by radiative transfer based reflectance imaging," Biomedical Optics Express, vol. 9, No. 5, pp. 2018-2094, Apr. 4, 2018.
(Continued)

*Primary Examiner* — Jamil Ahmed
(74) *Attorney, Agent, or Firm* — Stanek Lemon Crouse & Meeks, PA

(57) ABSTRACT

Multispectral imaging systems are provided including an illumination control module configured to image a sample and provide an imaging output sequence including images and data; a multi-spectral physiologic visualization (MSPV) module, a peripheral oxygen saturation ($SpO_2$) module and a physiologic status parameters (PSP) module configured to receive the imaging output sequence of the illumination control module simultaneously. The MSPV module is configured to provide real-time blood flow distribution visualization of a field of view (FOV) responsive to the received imaging output sequence. The $SpO_2$ module is configured to provide real-time $SpO_2$ information at a tissue surface level for the FOV responsive to the received imaging and output sequence. The PSP module is configured to derive status parameters in real-time from metadata associated with the
(Continued)

received imaging and output sequence of the FOV. The system further includes a processing engine configured to integrate and analyze the real-time blood flow distribution visualization, SpO$_2$ information and derived status parameters.

20 Claims, 18 Drawing Sheets

(51) Int. Cl.
    *G01J 3/36*     (2006.01)
    *A61B 5/00*     (2006.01)
    *A61B 5/1455*     (2006.01)
    *A61B 5/021*     (2006.01)
    *G01J 3/12*     (2006.01)

(52) U.S. Cl.
    CPC . *G01J 3/32* (2013.01); *G01J 3/36* (2013.01); *A61B 5/02108* (2013.01); *G01J 2003/1213* (2013.01); *G01J 2003/2826* (2013.01)

(58) Field of Classification Search
    CPC ........... G01J 2003/2826; A61B 5/0075; A61B 5/1455; A61B 5/02108
    See application file for complete search history.

(56) References Cited

U.S. PATENT DOCUMENTS

| | | | |
|---|---|---|---|
| 9,271,658 | B2 | 3/2016 | Ferguson, Jr. et al. |
| 9,480,424 | B2 | 11/2016 | Darty et al. |
| 10,058,256 | B2 | 8/2018 | Chen et al. |
| 10,205,892 | B2 | 2/2019 | Darty et al. |
| 10,390,718 | B2 | 8/2019 | Chen |
| 2011/0090325 | A1* | 4/2011 | Hauger ................ A61B 5/1455 348/77 |
| 2013/0012794 | A1 | 1/2013 | Zeng et al. |
| 2015/0078642 | A1 | 3/2015 | Fang |
| 2015/0282749 | A1 | 10/2015 | Zand et al. |
| 2016/0022181 | A1 | 1/2016 | Valsan et al. |
| 2016/0345835 | A1* | 12/2016 | Darty ..................... A61B 5/443 |
| 2017/0198349 | A1* | 7/2017 | Rice ....................... G06T 7/0012 |
| 2017/0274205 | A1* | 9/2017 | Chen ........................ A61N 1/08 |
| 2018/0092699 | A1* | 4/2018 | Finley ................ A61B 17/7062 |
| 2018/0153422 | A1 | 6/2018 | Watanabe |
| 2018/0234603 | A1 | 8/2018 | Moore et al. |
| 2019/0009387 | A1 | 1/2019 | Godavarty |

OTHER PUBLICATIONS

Radrich et al., "Quantitative multi-spectral oxygen saturation measurements independent of tissue optical properties," Journal of Biophotonics, pp. 83-99, Jan. 1, 2016.
International Search Report and Written Opinion, PCT/US2020/022295, dated Jun. 30, 2020, 12 pages.
Akobeng AK. Understanding diagnostic tests 3: Receiver operating characteristic curves. Acta Paediatr 2007; 96: 644-6screening47.
Alahdab F, Wang AT, Elraiyah TA, Maigor RD, Rizvi AZ, Lane MA, Prokop LJ, Montori VM, Conte MS, Murad MH. A systematic review for the screening for peripheral arterial disease in asymptomatic patients. J Vasc Surg 2015; 61: 42S-53S.
Bornstein JE, Munger JA, Deliz JR, Mui A, Cheng C, Kim S, Khaitov S, Chessin DB, Ferguson TB, Bauer JJ. Assessment of bowel end perfusion after mesenteric division: eye vs. SPY, 2018. J Surg Res 230:179-185.
Briers D DD, Hirst E, Kirkpatrick SJ, Larsson M, Steenbergen W, Stromberg T, Thompson OB. Laser speckle contrast imaging: Theoretical and practical limitations. Journal of biomedical optics 2013; 18: 066018.
Carreau A, El Hafny-Rahbi B, Matejuk A, Grilion C, Kieda C. Why is the partial oxygen pressure of human tissues a crucial parameter? Small molecules and hypoxia. J Cell Mol Med 2011; 15: 1239-1253.
Collins JA, Rudenski A, Gibson J, Howard L, O'Driscoll R. Relating oxygen partial pressure, saturation and content: The haemoglobin-oxygen dissociation curve. Breathe (Sheff) 2015; 11: 194-201.
Criqui MH, Aboyans V. Epidemiology of peripheral artery disease. Circulation research 2015; 116: 1509-1526.
Davies JL CC, Piek JJ. Coronary physiological parameters at a crossroads. EuroIntervention : journal of EuroPCR in collaboration with the Working Group on Interventional Cardiology of the European Society of Cardiology 2017; 13: 1-4.
De Bruyne B, Pijls NH, Kalesan B, Barbato E, Tonino PA, Piroth Z, Jagic N, Mobius-Winkler S, Rioufol G, Witt N, Kala P, MacCarthy P, Engstrom T, Oldroyd KG, Mavromatis K, Manoharan G, Verlee P, Frobert O, Curzen N, Johnson JB, Juni P, Fearon WF. Fractional flow reserve-guided pci versus medical therapy in stable coronary disease. N Engl J Med 2012; 367: 991-1001.
Ferguson TB Jr BA. Improving the quality and outcomes of coronary artery bypass grafting procedures. Expert Review of Cardiovascular Therapy 2016; 14: 617-631.
Ferguson TB Jr CC, Kim S, Jacobs K, Zeng Z, Zhu Z, Buch A, Basham J. Noninvasive quantification of blood flow in epicardial coronary arteries, coronary artery bypass grafts, and anastomoses. Innovations 2017; 12: 50-59.
Ferguson TB, Jr., Chen C, Babb JD, Efird JT, Daggubati R, Cahill JM. Fractional flow reserve-guided coronary artery bypass grafting: Can intraoperative physiologic imaging guide decision making? J Thorac Cardiovasc Surg 2013; 146: 824-835 e821.
Force USPST, Curry SJ, Krist AH, Owens DK, Barry MJ, Caughey AB, Davidson KW, Doubeni CA, Epling JW, Jr., Kemper AR, Kubik M, Landefeld CS, Mangione CM, Silverstein M, Simon MA, Tseng CW, Wong JB. Screening for peripheral artery disease and cardiovascular disease risk assessment with the ankle-brachial index: US preventive services task force recommendation statement. JAMA 2018; 320: 177-183.
Fowkes FG MG, Butcher I, et al. Ankle Brachial Index Collaboration. Ankle brachial index combined with framingham risk score to predict cardiovascular events and mortality. JAMA 2008; 300: 197-2008.
Fowkes FGR, Rudan D, Rudan I, Aboyans V, Denenberg JO, McDermott MM, Norman PE, Sampson UKA, Williams LJ, Mensah GA, Criqui MH. Comparison of global estimates of prevalence and risk factors for peripheral artery disease in 2000 and 2010: A systematic review and analysis. The Lancet 2013: 382: 1329-1340.
Gerhard-Herman MD, Gornik HL, Barrett C, Barshes NR, Corriere MA, Drachman DE, Fleisher LA, Fowkes FG, Hamburg NM, Kinlay S, Lookstein R, Misra S, Mureebe L, Olin JW, Patel RA, Regensteiner JG, Schanzer A, Shishehbor MH, Stewart KJ, Treat-Jacobson D, Walsh ME. 2018 aha/acc guideline on the management of patients with lower extremity peripheral artery disease: A report of the american college of cardiology/american heart association task force on clinical practice guidelines. Circulation 2017; 135: e726-e779.
Gerhard-Herman MD, Gomik HL, Barrett C, Barshes NR, Corriere MA, Drachman DE, Fleisher LA, Fowkes FG, Hamburg NM, Kinlay S, Lookstein R, Misra S, Mureebe L, Olin JW, Patel RA, Regensteiner JG, Schanzer A, Shishehbor MH, Stewart KJ, Treat-Jacobson D, Walsh ME. 2016 aha/acc guideline on the management of patients with lower extremity peripheral artery disease: Executive summary: A report of the american college of cardiology/american heart association task force on clinical practice guidelines. Circulation 2017; 135: e686-e725.
Gomaa D, Rodriquez D, Jr., Petro M, Blakeman TC, Branson RD. Impact of oxygenation status on the noninvasive measurement of hemoglobin. Mil Med 2017; 182: 87-91.
Guirguis-Blake JM, Evans CV, Redmond N, Lin JS. Screening for peripheral artery disease using the ankle-brachial index: Updated evidence report and systematic review for the us preventive services task force. JAMA 2018; 320: 184-196.
Hlatky MA, De Bruyne B, Pontone G, Patel MR, Norgaard BL, Byrne RA, Curzan N, Purcell I, Gutberlet M, Rioufol G, Hink U, Schuchlenz HW, Feuchtner G, Gilard M, Andrini D, Jensen JM, Hadamitzky M, Wilk A, Wang F, Rogers C, Douglas PS, Investi-

(56) References Cited

OTHER PUBLICATIONS gators P. Quality of life and economic outcomes of assessing fractional flow reserve with computed tomography angiography: The platform study. J Am Coll Cardiol 2015, 10.1016/j.jacc.2015.09.0151.
Jelani Qu, Petrov M, Martinez SC, Holmvang L, Al-Shaibi K, Alasnag M. Peripheral arterial disease in women: An overview of risk factor profile, clinical features, and outcomes. Curr Atheroscler Rep 2018; 20: 40.
Khan TH FF, Niazi K. Critical review of the ankle brachial index. Current Cardiology Reviews 2008; 4: 101-106.
Kim SK HL, McNames J. Tracking of rhythmical biomedical signals using the maxima a posteriori adaptive marginalized particle filter. British Journal of Health Informatics and Monitoring 2015; 2.
L Higgins G. What is the potential for false positive results in ankle brachial index measurements performed by emergency providers? Journal of General Practice 2013; 01.
Leach RM, Treacher DF. Oxygen transport: 2: Tissue hypoxia, BMJ 1998; 317(7169):1370-1373.
Lijmer JG HM, van den Dungen JJAM, Loonstra J, Smit AJ. Roc analyses of non-invasive tests for peripheral arterial disease. Ultrasound in Med and Biol 1996; 22: 391-398.
Loong T-W. Clinical review: Understanding sensitivity and specificity with the right side of the brain, BMJ 2003; 327: 716-719.
MacIntyre NR. Tissue hypoxia: implications for the respiratory clinician. Respiratory Care 2014. 59(10):1590-1596.
Martin DS, Khosravi M, Grocott M, Mythen MG. Concepts in hypoxia reborn. Crit Care 2010; 14(4):315.
McDermott M, Criqui MH. Ankle-brachial index screening and improving peripheral artery disease detection and outcomes. JAMA 2018; 320: 143-145.
McDermott MM. Lower extremity manifestations of peripheral artery disease: The pathophysiologic and functional implications of leg ischemia: Circulation research 2015; 116: 1540-1550.
Michiels C. Physiological and Pathological Responses to Hypoxia. Am J Physiol 2004; 164(6):1875-1882.
Pijls NHJ. Fractional flow reserve to guide coronary revascularization. Circulation Journal 2013; 77: 561-569.
S. CN, Han SH, Lim SH, Hong YS, Won JH, Bae JI, Jo J. Factors affecting the validity of ankle-brachial index in the diagnosis of peripheral arterial obstructive disease. Angiology 2010; 61: 392-396.
Semenza GL. Vascular Responses to Hypoxia and Ischemia. Arterioscler Thromb Vasc Biol 2010. April: 30(4):648-652.
Thabane L ML, Zhang S, Samaan Z, Marcucci M, Ye C, Thabane M, Giangregorio L, Dennis B, Kosa D, Debono VB, Dillenburg R, Fruci V, Bawor M, Lee J, Wells G, Goldsmith CH. A tutorial on sensitivity analyses in clinical trials: The what, why, when and how. BMC Medical Research Methodology 2013; 13: 1-12.
Tonino PAL dBB, Pijls NHJ, Siebert U, Ikeno F, van't Veer M, Klauss V, Manoharan G, Engstrom T, Oldroyd KG, Ver Lee PN, MacCarthy PA, Fearon WA, for the FAME Study Investigators. Fractional flow reserve versus angiography for guiding percutaneous coronary intervention. N Engl J Med 2009; 360: 213-224.
Vaz PG, Humeau-Heurtier A, Figueiras E, Correia C, Cardoso J. Laser speckle imaging to monitor microvascular blood flow: A review. IEEE Rev Biomed Eng 2016; 9: 106-120.
White CJ. Cookbook medicine is the recipe for successfully managing patients with pad. J Am Coll Cardiol 2018; 72: 1012-1014.
Wikstrom J HT, Johansson L, Lind L, Ahlstrom H. Ankle brachial index < 0.9 underestimates the prevalence of peripheral artery occlusive disease assessed with whole-bodu magnetic resonance angiography in the elderly. Acta Radiologica 2008; 49: 143-149.
Wikstrom J, Hansen T, Johansson L, Ahlstrom H, Lind L. Lower extremity artery stenosis distribution in an unselected elderly population and its relation to a reduced ankle-brachial index. J Vasc Surg 2009; 50: 330-334.
A. A. Kamshilin, M. A. Volynsky, O. Khayrutdinova, D. Nurkhametova, L. Babayan, A. V. Amelin, O. V. Mamontov, and R. Giniatullin, "Novel capsaicin-induced parameters of microcirculation in migraine patients revealed by imaging photoplethysmography." The journal of headache and pain 19, 43 (2018).
A. Jubran, "Pulse oximetry," Critical care 19, 272 (2015).
A. Nouvong, B. Hoogwerf, E. Mohler, B. Davis, A. Tajaddini, and E. Medenilla, "Evaluation of Diabetic Foot Ulcer Healing With Hyperspectral Imaging of Oxyhemoglobin and Deoxyhemoglobin," Diabetes Care 32, 2056-2061 (2009).
C. Chen, J. Q. Lu, K. Li, S. Zhao, R. S. Brock, and X. H. Hu, "Numerical study of reflectance imaging using a parallel Monte Carlo method," Med. Phys. 34, 2939-2948 (2007).
Criqui MH, Aboyans V. Epidemiology of peripheral artery disease. Circulation research 2015; 116: 1509-1525.
D. Alvarez, R. Hornero, J. V. Marcos, and F. d. Campo, "Multivariate Analysis of Blood Oxygen Saturation Recordings in Obstructive Sleep Apnea Diagnosis," IEEE Transactions on Biomedical Engineering 57, 2816-2824 (2010).
G. C. Gurtner, G. E. Jones, P. C. Neligan, M. I. Newman. B. T. Phillips, J. M. Sacks, and M. R. Zenn, "Intraoperative laser angiography using the SPY system: review of the literature and recommendations for use," Annals of Surgical Innovation and Research 7, 1 (2013).
J. Allen, "Photoplethysmography and its application in clinical physiological measurement," Physiological Measurement 28, R1-R39 (2007).
J. Q. Lu, C. Chen, D. W. Pravica, R. S. Brock, and X. H. Hu, "Validity of a closed-form diffusion solution in P1 approximation for reflectance imaging with an oblique beam of arbitrary profile," Med. Phys. 35, 3979-3987 (2008).
M. R. Future, "Perfusion Imaging Market Research Report—Global Forecast till 2024," (WantStats Research and Media Pvt Ltd, 2019). Notification of Transmittal of the International Search Report and the Written Opinion of the International Searching Authority, or the Declaration PCT/US2019/035792, dated Sep. 10, 2019, 11 pages.
P. Tian, C. Chen, J. Jin, H. Hong, J. Q. Lu, and X.-H. Hu, "Quantitative characterization of turbidity by radiative transfer based reflectance imaging," Biomed. Opt. Express 9, 2081-2094 (2018).
P. Tian, X. Chen, J. Jin, J. Q. Lu, X. Liang, and X. H. Hu, "A stochastic model for quantifying effect of surface roughness on light reflection by diffuse reflectance standards," Opt. Eng. 67 (in press) (2018).
R. Bi, J. Dong, C. L. Poh, and K. Lee, "Optical methods for blood perfusion measurement: theoretical comparison among four different modalities," J. Opt. Soc. Am. A 32, 860-866 (2015).
X. Chen, Y. Feng, J. Q. Lu, X. Liang, J. Ding, Y. Du, and X. H. Hu, "Fast method for inverse determination of optical parameters from two measured signals," Optics letters 38, 2095-2097 (2013).
Y. An, Y. Kang, J. Lee, C. Ahn, K. Kwon, and C. Choi, "Blood flow characteristics of diabetic patients with complications detected by optical measurement," BioMedical Engineering OnLine 17, 25 (2018).
Y. Sun, and N. Thakor, "Photoplethysmography Revisited: From Contact to Noncontact, From Point to Imaging," IEEE Trans Biomed. Eng. 63, 463-477 (2016).
International Search Report and Written Opinion, PCT/US2019/049489, dated Jun. 3, 2020.
International Search Report, PCT/US2020/024645, dated Sep. 2, 2020, 9 pages.
HyperView™, HyperMed Medical Spectral Imaging, 2017, 5 pages.

* cited by examiner

MSPV TISSUE PERFUSION IMAGE

SpO2 IMAGE

SpO2 = 98%

SpO2 = 91%

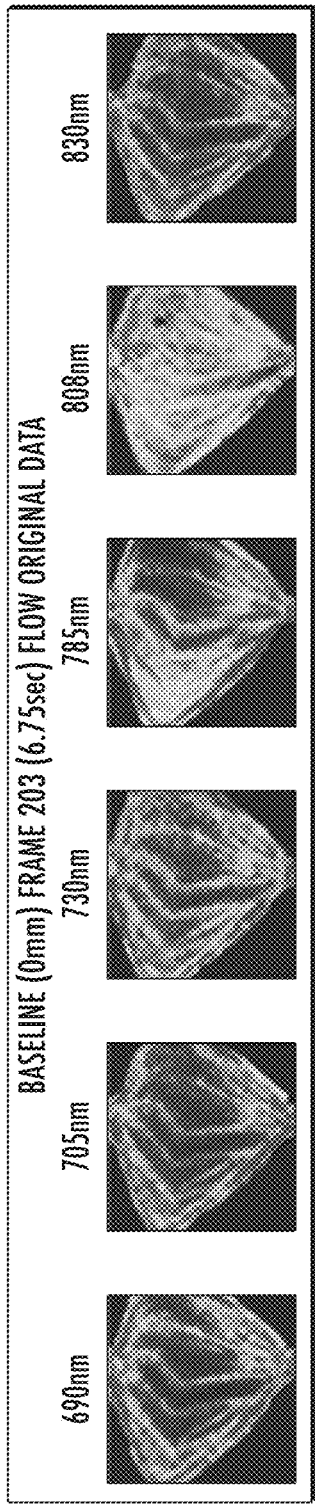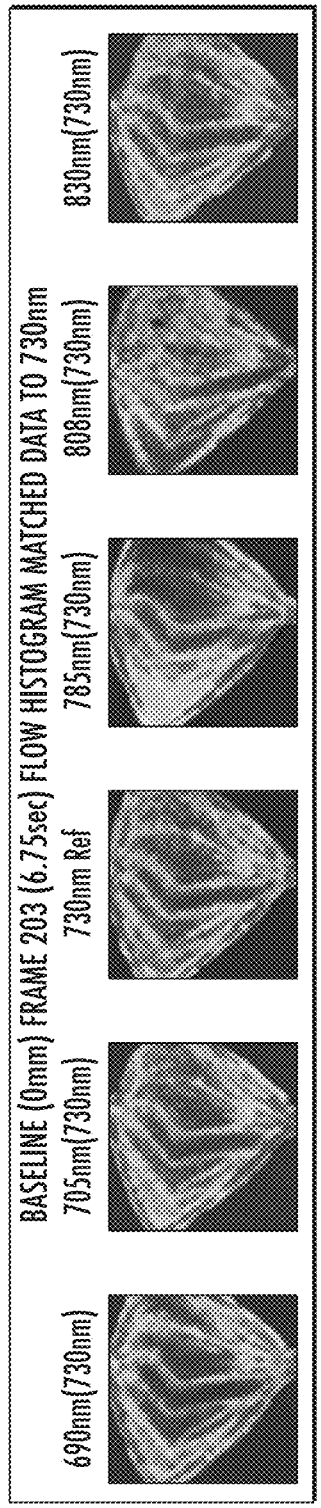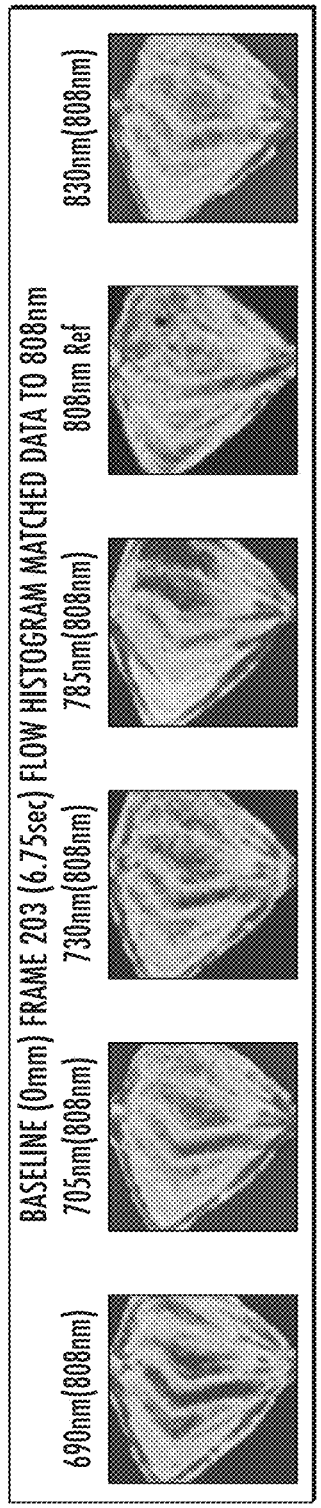

SYSTEMS FOR DETECTING VASCULAR AND ARTERIAL DISEASE IN ASYMPTOMATIC PATIENTS AND RELATED METHODS

CLAIM OF PRIORITY

The present application claims priority to U.S. Provisional Application No. 62/727,293, filed Sep. 5, 2018, entitled Methods for Detecting Vascular and Arterial Disease in Asymptomatic Patients, the contents of which is hereby incorporated herein by referenced as if set forth in its entirety.

GOVERNMENT SUPPORT

This invention was made with government support under HL133633-01 awarded by the National Institutes of Health. The government has certain rights in the invention.

FIELD

The present inventive concept relates generally to imaging systems and, more particularly, to using various systems to detect diseased in atypical subjects.

BACKGROUND

Peripheral vascular disease (PVD) and peripheral arterial disease (PAD) are and enormous healthcare burden in the United States. An estimated 8.0-8.5 million (M) (approximately 1 in 20) US adults have PAD. The associated risks of adverse cardiovascular events and limb-related outcomes are markedly increased in these patients, resulting in a dramatic excess morbidity and mortality.

PAD can be detected through, for example, a noninvasive measurement of the ankle-brachial index (ABI). This conventional ABI (cABI) test correlates the measured ankle/brachial systolic blood pressure threshold ratio with the likelihood of an anatomic stenosis compromising blood inflow to the lower extremities. But while cABI has been validated as an accurate test in symptomatic patients with PAD, its performance in asymptomatic patients has been questioned. Unfortunately, only approximately 10% of patients with PAD have classic symptoms of claudication; the rest are asymptomatic (50%) or have atypical symptoms (40%). A better evaluation process for these asymptomatic/atypical patients is an acute unmet need in US healthcare.

SUMMARY

Some embodiments of the present inventive concept provide multispectral imaging systems including an illumination control module configured to image a sample and provide an imaging output sequence including images and data; a multi-spectral physiologic visualization (MSPV) module, a peripheral oxygen saturation ($SpO_2$) module and a physiologic status parameters (PSP) module configured to receive the imaging output sequence of the illumination control module simultaneously. The MSPV module is configured to provide real-time blood flow distribution visualization of a field of view (FOV) responsive to the received imaging output sequence. The $SpO_2$ module is configured to provide real-time $SpO_2$ information at a tissue surface level for the FOV responsive to the received imaging and output sequence. The PSP module is configured to derive status parameters in real-time from metadata associated with the received imaging and output sequence of the FOV. The system further includes a processing engine configured to integrate and analyze the real-time blood flow distribution visualization, $SpO_2$ information and derived status parameters.

In further embodiments, the system may further include a user interface configured to display the integrated and analyzed real-time blood flow distribution visualization, $SpO_2$ information and derived status parameters. The MSPV module may be configured to provide the blood flow and distribution data in form of a video. The $SpO_2$ module may be configured to provide the $SpO_2$ information in a still image form. The PSP module may be configured to provide the status parameters in graphic form.

In still further embodiments, the system may further include a database/storage module. The MSPV module and the PSP module may be configured to store the real-time blood flow distribution visualization and the status parameters in one or more matrix files in the database/storage module. The $SpO_2$ module may be configured to store the $SpO_2$ information as individual value data for each pixel in the FOV and as an averaged per pixel deoxyhemoglobin/oxyhemoglobin ratio for the FOV in the database/storage module.

In some embodiments, the processing engine is further configured to process data stored in the database/storage module using artificial intelligence (AI) algorithms and deep learning algorithms.

In further embodiments, data stored in the database/storage module may be de-identified having no identifiers in digital datasets.

In still further embodiments, the imaging output sequence may be an imaging output sequence of from about 10 to about 12 seconds.

In some embodiments, the status parameters may include one or more of tissue perfusion (TP), dynamic change in tissue perfusion (DCTP), tissue ischemia (TI), systolic, diastolic and mean blood pressure (BP), heart rate (HR), and relative index of sympathetic tone.

In further embodiments, the illumination control may include first and second optical head units (OHUs), each of the first and second OHUs being configured to a corresponding first and second focal length for a first and second imaging output sequence, respectively. The first OHU may have the first focal length for the imaging output sequence and may be configured to illuminate a first portion of sample and provide the first imaging output sequence to the MSVP module, the $SpO_2$ module and the PSP module. The second OHU may have the second focal length for the imaging output sequence and may be configured to illuminate a second portion of sample, different from the first portion, and provide the second imaging output sequence to the MSVP module, the $SpO_2$ module and the PSP module.

In still further embodiments, the first and second OHUs may be coupled to first and second flexible attachments such that first and second OHUs may be positioned at the first and second portions of the sample, respectively.

In some embodiments, the first and second OHUs may be configured to simultaneously acquire from about 20 to about 25 seconds of data and provide the acquired data to the MSVP module, the $SpO_2$ module and the PSP module. The processing engine may be further configured to analyze data from the MSVP module, the $SpO_2$ module and the PSP module. The system may further include a physical display, the physical display being configured to display results from the processing engine in real-time.

In further embodiments, the illumination control may be positioned on a mobile cart and wherein the mobile cart may be configured to be repositioned to obtain image sequences from other portions of the sample different from the first and second portions.

Still further embodiments of the present inventive concept provide related methods.

BRIEF DESCRIPTION OF THE DRAWINGS

FIGS. 3A through 3C illustrate is a series of images illustrating flow data in accordance with some embodiments of the present inventive concept.

DETAILED DESCRIPTION

Figure 1:
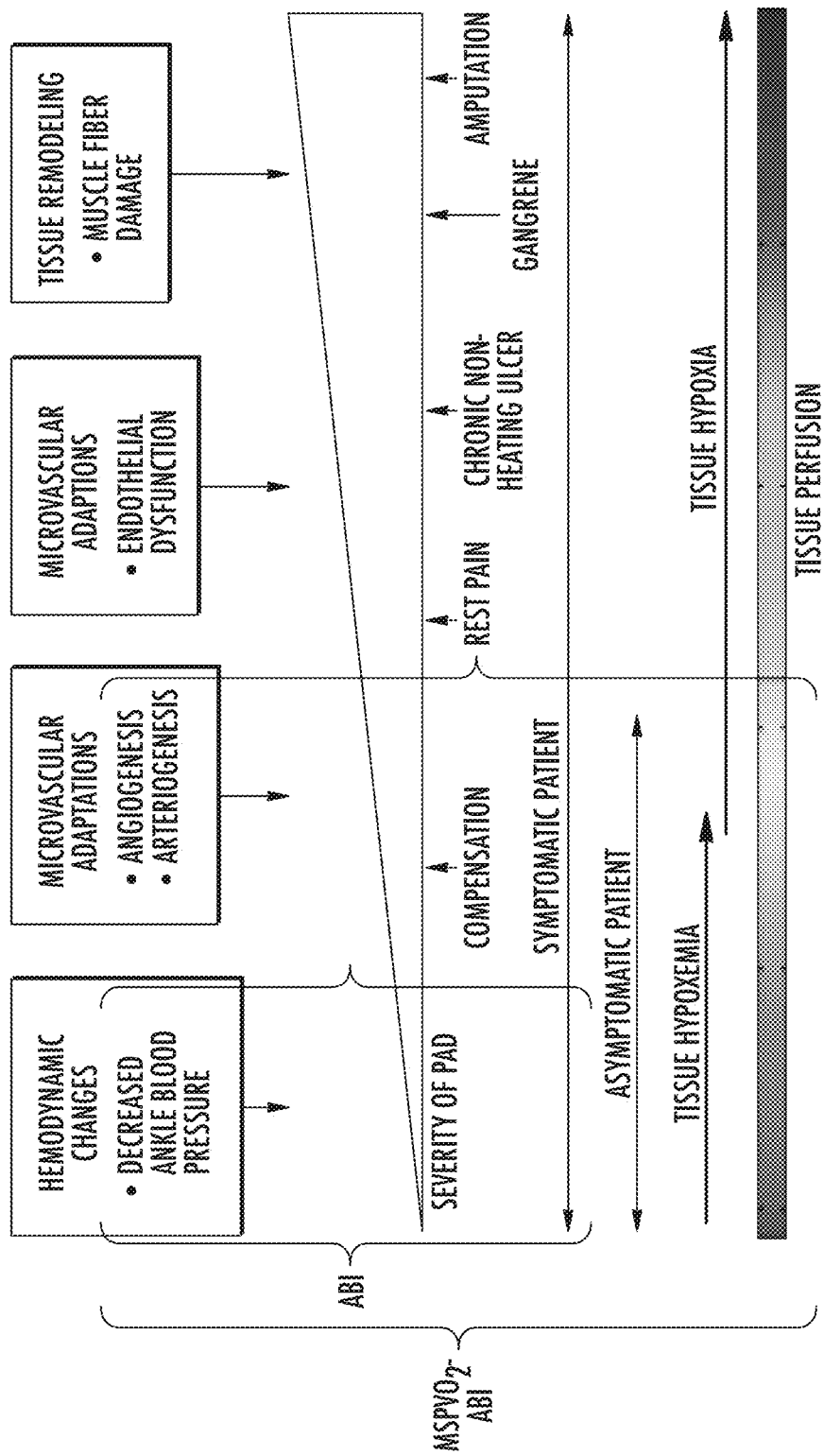
FIG. 1 is a diagram illustrating the relentless progression of peripheral arterial disease.

Embodiments of the present inventive concept will now be described more fully hereinafter with reference to the accompanying Figures, in which preferred embodiments of the inventive concept are shown. This inventive concept may, however, be embodied in many different forms and should not be construed as limited to the embodiments set forth herein. Like numbers refer to like elements throughout. In the Figures, layers, regions, elements or components may be exaggerated for clarity. Broken lines illustrate optional features or operations unless specified otherwise.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y." The term "about" means the numerical value can vary by plus or minus ten percent.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the inventive concept. The sequence of operations (or steps) is not limited to the order presented in the claims or Figures unless specifically indicated otherwise.

Spatially relative terms, such as "under", "below", "lower", "over", "upper" and the like, may be used herein for ease of description to describe one element or feature's relationship to another element(s) or feature(s) as illustrated in the Figures. It will be understood that the spatially relative terms are intended to encompass different orientations of the device in use or operation in addition to the orientation depicted in the Figures. For example, if a device in the Figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

As will be appreciated by one of skill in the art, embodiments of the present inventive concept may be embodied as a method, system, data processing system, or computer program product. Accordingly, the present inventive concept may take the form of an embodiment combining software and hardware aspects, all generally referred to herein as a "circuit" or "module." Furthermore, the present inventive concept may take the form of a computer program product on a non-transitory computer usable storage medium having computer usable program code embodied in the medium. Any suitable computer readable medium may be utilized including hard disks, CD ROMs, optical storage devices, or other electronic storage devices.

Computer program code for carrying out operations of the present inventive concept may be written in an object-oriented programming language such as Matlab, Mathematica, Java, Smalltalk, C or C++. However, the computer program code for carrying out operations of the present inventive concept may also be written in conventional procedural programming languages, such as the "C" programming language or in a visually oriented programming environment, such as Visual Basic.

It will be understood that some embodiments of the present inventive concept implemented in Matlab may provide improved processing speeds in accordance with some embodiments of the present inventive concept.

Certain of the program code may execute entirely on one or more of a user's computer, partly on the user's computer, as a standalone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The inventive concept is described in part below with reference to flowchart illustrations and/or block diagrams of methods, devices, systems, computer program products and data and/or system architecture structures according to embodiments of the inventive concept. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

As used here, "Multispectral Laser Imaging (MSLI)" refers to imaging techniques using two or more wavelengths in accordance with some embodiments of the present inventive concept. For example, MSLI techniques are discussed in commonly assigned U.S. patent Ser. No. 10/058,256 entitled Multi-Spectral Laser Imaging (MSLI) Methods and Systems for Blood Flow and Perfusion Imaging and Quantification, to Chen et al., the disclosure of which is hereby incorporated herein by reference as if set forth in its entirety.

As used herein, "real-time" refers to provision of data within a very short amount of time, for example, milliseconds, so as to appear as if the data was provided immediately upon request or activation of light sources.

The figures are shown in a gray scale as colored photographs are not filed with patent applications. Thus, it is understood that some of the details of the images provided herein are lost in the black and white images.

As discussed in the background, an improved evaluation process for asymptomatic/atypical patients is desired. In other words, as more knowledge is obtained with respect to various conditions, for example, these conditions may be diagnosed before the patient actual experiences the symtoms associated with the particular condition. In other circumstances, the patient may not be experiencing typical symptoms associated with a particular condition, but using an improved evaluation process in accordance with embodiments discussed herein, the patient may be properly diagnosed before the condition progresses. This improved evaluation process is particularly important with respect to peripheral arterial disease (PAD) and peripheral vascular disease (PVD) as will be discussed further herein. Although, it will be understood that embodiments of the present inventive concept are not limited to a PAD and PVD evaluation. Embodiments of the present inventive concept are also rely upon the framework of PVD itself and the importance of clinical evaluation/monitoring technology solution in accordance with embodiment of the present inventive concept will be discussed.

The United States Preventive Services Task Force (USPSTF) has endorsed conventional ankle-brachial index (cABI) testing in symptomatic patients, but recently did not support its use for screening asymptomatic patients. As discussed above, a cABI test correlates the measured ankle/ brachial systolic blood pressure threshold ratio with the likelihood of an anatomic stenosis compromising blood inflow to the lower extremities of the subject. This gap in the initial evaluation of patients who have a non-classic (asymptomatic) presentation of, for example, PAD, represents an important healthcare improvement opportunity, both diagnostically and potentially therapeutically. The data cited by the USPSTF to reach their recommendations clearly document the limited applicability of the standard ABI test in the asymptomatic setting. cABi is a single component test, i.e., blood pressure ratio yielding a percent of anatomic stenosis, with a specificity, i.e., healthy people identified as not having PAD, nearly equivalent to that seen with symptomatic patients, but with a dramatic fall in the sensitivity, i.e., how many patients with PAD are correctly identified, from nearly 80 percent to 20 percent in the asymptomatic patients undergoing cABI testing.

When this screened asymptomatic PAD population is analyzed, it is the patient co-morbidities that appear to be driving down this sensitivity. Patients with diabetes drive down the sensitivity of ABI testing in symptomatic patients from greater than 80% to less than 50%, and elderly patients affected the false negative cABI rate almost as much as diabetes. These findings have led investigators to argue for other supplemental investigations in these clinically uncertain circumstances. A recent evolution is the strong clinical suspicion that patients with high risks and/or clinical manifestations of cerebrovascular and cardiovascular atherosclerotic disease are at increased risk for PAD, even if the PAD is asymptomatic. Cigarette smoking, for example, increases the risk of PAD up to 6 times baseline risk. This disease association has led other organizations to recommend ABI testing in "higher cardiovascular risk" asymptomatic patients despite the inferior performance of cABI, and where the increase in false positive results leads to an increase in normal diagnostic angiograms downstream.

As a single component test, modification of how the cABI is performed is unlikely to improve these sensitivity results. Rather, the fact that the concomitant disease processes (DM, severe smoking, aging factors) seem to be driving the sensitivity outcomes is noteworthy. Moreover, these findings suggest that concomitant evaluation of the end-organ tissue vascular status of patients with these co-morbid disease processes might improve the utility and possibly accuracy of ABI-type testing in this asymptomatic group of PAD patients.

From a cardiovascular disease perspective, it is logical to equate the following:

(1) a single component screening test (i.e., cABI blood pressure ratio result less than 0.90 equates to percent anatomic stenosis) leading to subsequent diagnostic angiography (greater than 50% stenosis) leading to intervention; and (2) the 'pre-physiologic' era in Stable Ischemic Heart Disease (SIHD), where an abnormal electrocardiogram (ECG) led to diagnostic angiography (greater than 50% stenosis) which led to intervention. Both are fundamentally anatomy-based strategies. In both circumstances, therapeutic decisions are/were principally based upon anatomic criteria, for example, percent anatomic stenosis, alone, even in asymptomatic or marginally symptomatic patients. While this approach in SIHD was standard of care for almost 40 years, the advent of physiologic evaluation and elucidation of the critical importance of functional stenosis and end-organ tissue metabolism has changed this standard of care. Pre-intervention physiologic evaluation with fractional flow reserve (FFR), or instant wave-free ratio (iFR), and more recently fractional flow reserve-computed tomography (FFR-CT) has transformed the evaluation and management of patients with SIHD and, in particular, for atypical presentations of SIHD.

Embodiments of the present inventive concept apply this same rationale to asymptomatic PAD patients. By inference, this would involve extending the single component cABI test (→anatomic information) with additional testing that informs about the physiology of the end-organ tissues that are being perfused by the potentially diseased arterial conduits. This approach may approve initial evaluation of the asymptomatic and/or complex PAD patient, and perhaps begin to address this unmet need in PAD.

Accordingly, some embodiments of the present inventive concept may streamline time and effort required to perform the exacting cABI testing, a procedure which even in experienced hands can take 20-30 minutes to do a bilateral evaluation. In stark contrast, embodiments of the present inventive concept may take less than 1 minute, for example, 10-20 seconds to collect the data simultaneously or serially from both the upper and lower extremities and may be repeated as often as needed for measurement validation or improved accuracy. Some embodiments of the present inventive concept may also perform testing in a non-contact, non-invasive form factor that is reliable, robust, safe and simple in a footprint suitable for vascular clinic use. As used herein, "non-contact" does not imply that there will no contact with a patient or subject, just minimal contact, i.e. no dyes or probes inserted near test area etc. Some embodiments of the present inventive concept provide new end-organ physiology data, in conjunction with relative pressure data that may be equivalent to the cABI relative results and may lead to a better understanding of the interactions and influences between arterial inflow insufficiency and the end-organ physiologic consequences much earlier in the continuum of PAD and PVD. As used herein, "end-organ" refers to a target organ.

It will be understood that although embodiments of the present inventive concept are discussed with respect to PAD and PVD, embodiments of the present inventive concept are not limited to these particular conditions. Embodiments discussed herein can be used for any condition the teachings thereof lend itself to without departing from the scope of the present inventive concept.

Referring now to FIG. 1, a block diagram illustrating the relentless progression of PAD will be discussed. FIG. 1 conceptually illustrates both the conventional ABI method and a multi-spectral physiologic (MSPV) $O_2$ ABI (MSPVO$_2$-ABI) methods in accordance with embodiments of the present inventive concept. Referring to FIG. 1, cABI is applicable to symptomatic patients with anatomic disease. In stark contrast, MSPVO$_2$-ABI in accordance with embodiments of the present inventive concept can be used to encompasses the anatomic disease captured by cABI, but also captures end-organ tissue data on real-time perfusion and real-time peripheral oxygen tissue status, over a broader range of asymptomatic and atypical patients.

In particular, as illustrated in FIG. 1, although symptomatic patients may experience one or more of hemodynamic changes (decreased ankle blood pressure); microvascular adaptations (angiogenesis or arteriogenesis); microvascular adaptations (endothelial dysfunction) and tissue remodeling (muscle fiber damage) depending on the severity of PAD, an asymptomatic patient or an atypical patient may not experience any of these conditions. Thus, the asymptomatic or atypical patient may go undiagnosed until the condition progresses to a dangerous point. In particular, the earlier the diagnosis, the less severe the disease, the progression being compensation, rest pain, chronic non-healing ulcer, gangrene and amputation. Using MSPVO$_2$-ABI in accordance with embodiments discussed herein may allow symptomatic, asymptomatic and atypical patients all to be diagnosis before the disease full progresses.

The scientific support for cABI as the initial diagnostic test for patients with symptomatic claudication up to rest pain is robust. The difficulty lies in those patients who don't fit the classic PAD mold. For example, asymptomatic people with an ABI less than 0.90 have poorer functional performance and quality of life compared to a sedentary, asymptomatic age-matched non-PAD group. This lack of diagnostic inertia deprives these patients from the benefits of Guideline Directed Medical Therapies, which in symptomatic patients prevent cardiovascular events. Furthermore, effective PAD evaluation of patients with co-morbid cardiovascular and cerebrovascular disease, but no PAD symptoms, is important. Moreover, a test for evaluating non-specific leg symptoms common in elderly patients, particularly in women, with a risk for PAD is also desired. There currently trials being performed for PAD. However, none of these trials used ABI alone to screen for PAD, but rather includes other manifestations of the effects of vascular disease as well. A single diagnostic accuracy study demonstrated that the ABI has poor sensitivity for detecting PAD in unselected populations. That said, the European Society of Cardiology and the AHA/ACC, in conflict with the USPSTF recommendations, endorse screening for PAD with ABI in elderly patients and patients with high cardiovascular disease (CVD) risk (DM, smoking history, hyperlipidemia, hypertension), or Family History of PAD, or age greater than 50 with one or more CVD or PAD disease risk factors. A strategy to broaden the applicability and efficacy of the fundamentals of the ABI testing is needed.

Some embodiments of the present inventive concept capture the principles of ABI measurement and anatomy definition, and couple it with critically important physiologic information about perfusion and oxygen metabolism in the end-organ tissues using Multi-Spectral Physiologic Visualization (MSPV). MSPV is an imaging platform using multi-spectral imaging acquisition and laser speckle contrast analyses to visualize and quantify blood flow distribution—blood flow in vessels and perfusion in tissues—and physiology. MSPV is discussed, for example, in commonly assigned U.S. Pat. Nos. 9,271,658; 9,226,673; and 10,058,256, the contents of which are hereby incorporated herein by reference as if set forth in their entirety. A comprehensive hardware and software solution, MSPV uses multi-spectral imaging acquisition (multiple wavelength illumination, reflectance capture) and laser spectral contrast analyses. Since dynamic physiology is visualized from time zero (to), image acquisition time may only be 10-20 seconds. The MSPV analysis is executed from the imaging acquisition data in real-time and, thus, the analyzed MSVP video data are presented to the provider in true real-time. By "fusing" anatomic detail with this physiology, the MSPV analysis imaging content has exceptional fidelity. MSPV is non-contact, non-invasive (no dyes or contrast agents), doesn't use ionizing radiation, and is minimal risk to patients or providers even with multiple imaging acquisition episodes. The scientific rigor and transparency of the MSPV technology solution is fully validated by the recent (Dec. 14, 2018) federal drug administration (FDA) approval of the first clinical form factor, called iCertainty. In open surgical procedures, the iCertainty MSPV form factor images and relatively quantifies blood flow distribution over an entire 9 cm×9 cm field of view (FOV) of surgical tissues. In a PAD evaluation, this may include the distal lower extremities. Thus, MSVP corresponds to the "MSPV" portion of MSPVO$_2$-ABI in accordance with embodiments of the present inventive concept.

In addition to perfusion, the metabolic progression of normoxia→hypoxemia→hypoxia (FIG. 1) at the tissue level is critical to complex PAD evaluation. In PAD, hypoxemia is most often a relative systemic condition, i.e., pulmonary disease and vascular reactivity from smoking, and mostly independent of hemoglobin delivery, while tissue hypoxia in this setting is primarily an oxygen delivery problem coupled with local tissue metabolism abnormalities, some of which are a biologic response to the hypoperfusion and hypoxia. To this end, embodiments of the invention provide an optimal configuration for non-invasive, non-contact determination of peripheral oxygen saturation (SpO$_2$) and local hemoglobin concentration ([Hgb]) in tissues, also in real-time. Embodiments of the present inventive concept discuss an MSPV platform that incorporates SpO$_2$ into the MSPV platform. Since perfusion cannot be inferenced from a relative 'map' of SpO$_2$ distribution, this MSPV-O$_2$ approach is unique in providing real-time perfusion and tissue oxygenation data simultaneously across the entire FOV which is typically 9 cm×9 cm, thus, providing the "O$_2$" portion of MSPVO$_2$-ABI.

Once real-time blood flow distribution physiology (MSPV) is captured, the analysis of MSPV metadata reveals the physiologic drivers of that blood flow distribution, Physiologic Status Parameters (PSPs). PSPs include, for example, tissue perfusion (TP), dynamic change in tissue perfusion (DCTP), tissue ischemia (TI), systolic, diastolic and mean blood pressure (BP), heart rate (HR), and relative index of sympathetic tone. Some embodiments correlate these PSP determinations derived entirely non-invasively with sphygmomanometer measurements of BP and ECG measurement of HR.

Together, these components (perfusion, peripheral oxygenation, and cardiovascular hemodynamics) can be used to provide a method of assessing atypical patients with PAD and PVD beyond ABI. Some embodiments provide an entirely new technologic solution, MSPVO$_2$-ABI, in an entirely new form factor that is real-time, accessible, effective and minimally obtrusive in care delivery.

While ABI may remain the gold standard in symptomatic patients with PAD, the MSPVO$_2$-ABI technology as discussed herein may provide a new strategy for asymptomatic PAD patients, including those with other risk factors for cardiovascular and cerebrovascular disease. In clinical practice, the test can be much simpler and straightforward to conduct, take less than half the time of conventional ABI, and result in a digital output that can be readily stored, transmitted, and captured in an ongoing data construct. The multi-factorial data output can be quantified in all three components for simple, imaging-based interpretation.

Development and effectiveness validation of this novel testing approach may have an enormous impact on PAD evaluation. Among people with an cABI less than 0.90, the prevalence of asymptomatic PAD varies from 20 percent to 60 percent, and in this same cABI set the prevalence of atypical leg symptoms ranges from 30 percent to 50 percent. The solution to this clinical dilemma is to modify the testing procedure to better meet the clinical nuances of the patient populations being evaluated. Improvements in the non-invasive ability to differentiate patients with and without PAD who fall into these atypical categories may reduce, or possibly prevent, overuse of unnecessary diagnostic and therapeutic approaches, and more importantly help avoid under-diagnosis of actual disease and disease progression, which may result in the truly adverse complications and outcomes that can accompany PAD.

Some embodiments of the present inventive concept may illustrate that the combination of anatomic and physiologic data to diagnose and determine optimal intervention strategies for patients with PAD provides the same new knowledge and clinical benefit as these same developments in SIHD.

Figure 10:
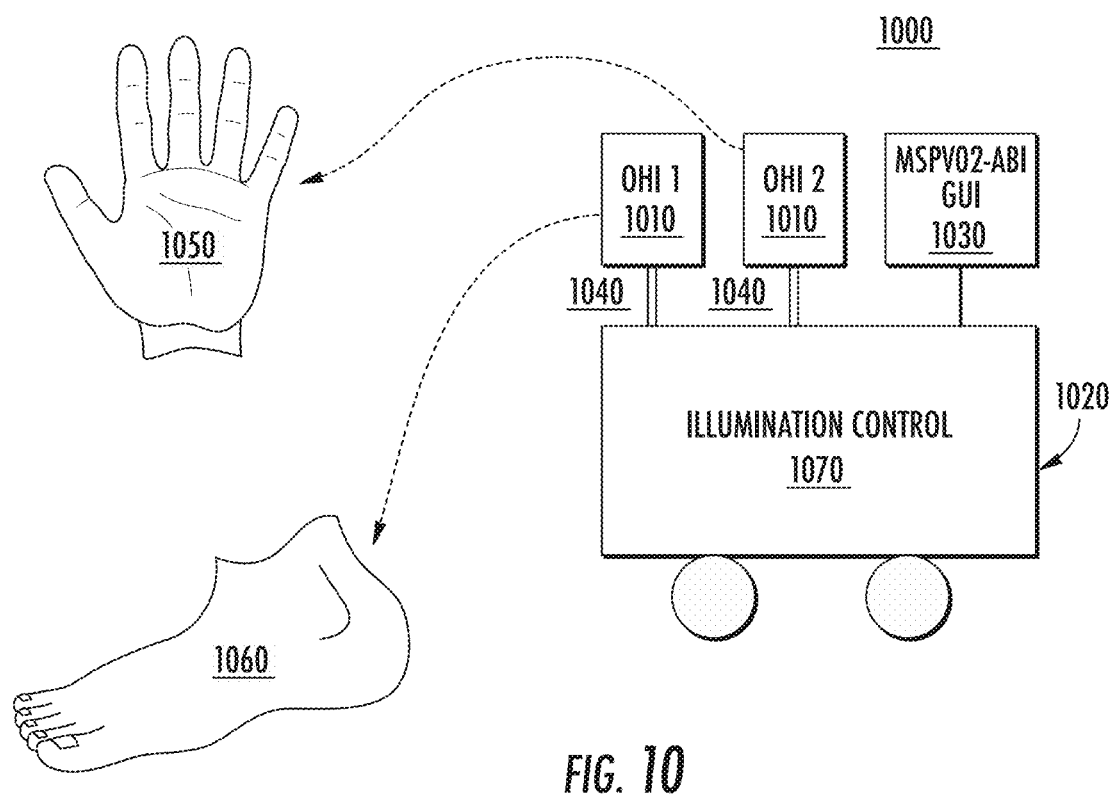
FIG. 10 is a block diagram illustrating an example system in accordance with embodiments of the present inventive concept.

Some embodiments of the present inventive concept provide a distinctly innovative solution compared with other low-end, non-radiologic cardiovascular evaluation measurement approaches. As illustrated in FIG. 10, some embodiments of the present inventive concept provide a simple configuration for the $MSPVO_2$-ABI system 1000 including multiple, for example, two (2), imaging optical head units (OHU) 1010, mounted on a mobile cart 1020 with a mounted high-definition screen and computer graphical user interface (GUI) 1030. Flexible but stable attachments 1040 facilitate easy positioning of each OHU 1010 at the correct focal length for accurate imaging sequence acquisition. In the supine patient at rest, the first OHU images the palmar surface of the hand and digits 1050; the second OHU 1040 images the ipsilateral posterior tibial or dorsalis pedis region of the foot/ankle 1060. No sphygmomanometers or hand-held dopplers are necessary. The $MSPVO_2$-ABI system 1000 is entirely non-contact and non-invasive. Simultaneous imaging acquisition from both OHUs 1010 captures typically 20-25 seconds of data. The analyzed results are immediately displayed on the GUI 1030, and repeat imaging, if necessary, is straightforward. The cart 1020 may be re-positioned on the other side of the patient, and imaging acquisition may be completed for that side. The startup, setup, OHU positioning and imaging of both sides may be less than 10 minutes/patient.

By capturing simultaneous anatomy-based and physiology-based integrated data, embodiments of the present inventive concept provide insights into whether the "functional anatomy" concepts and principles determined in SIHD are present in PVD.

As discussed, some embodiments of the present inventive concept provide $MSPVO_2$-ABI methods and systems that provide non-invasive visualization and quantification of tissue perfusion; peripheral oxygen saturation, and PSP determination of systolic BP threshold and HR. Further, methods and systems discussed herein are built upon MSPV technology for visualization and quantification of blood flow distribution. As discussed MSPV is a combined hardware and software solution, with illumination by multiple lasers, a multi-sensor camera, and real-time analysis and display of the data in video format, depicting relative blood flow distribution in target tissues within the 9 cm (diameter) FOV. MSPV can be provided as a real-time surgical and clinic blood flow distribution imaging technology platform.

Figure 2A:
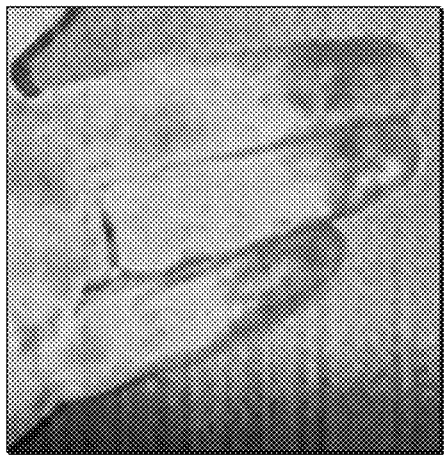
FIGS. 2A through 2D illustrates a series of images under conditions of similar perfusion, FIGS. 2A and 2B illustrating Multi-Spectral Physiologic Visualization (MSPV) Tissue Perfusion and FIGS. 2C and 2D illustrating corresponding $SpO_2$ images in accordance with embodiments of the present inventive concept.
Figure 2B:
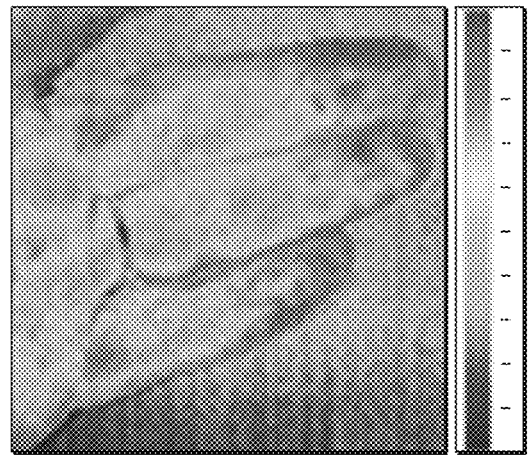
Figure 2C:
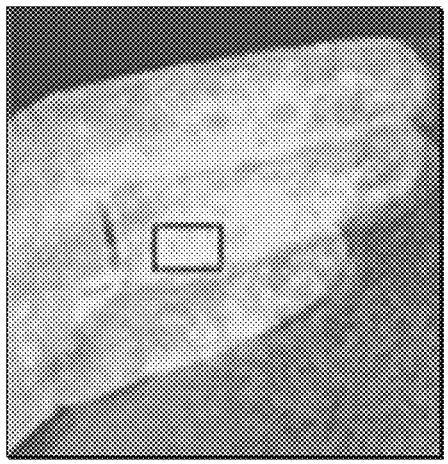
Figure 2D:
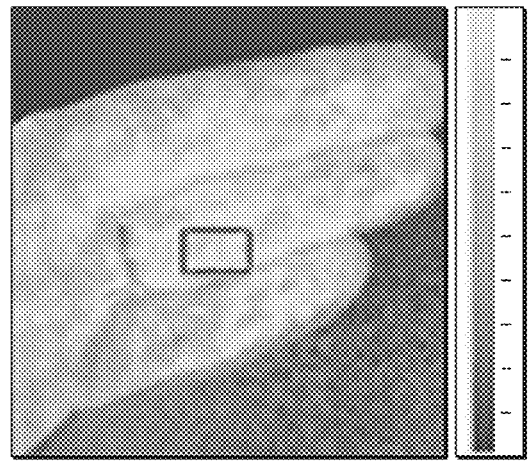

In some embodiments of the present inventive concept, to measure in real-time, the $SpO_2$ of tissues non-invasively and using an MSPV imaging platform, existing laser diodes of different wavelengths may be interfaced with an MSPV system. This configuration was used to perform initial studies to demonstrate combining MSPV imaging acquisition with $SpO_2$ and [Hgb] determination in the same FOV in accordance with embodiments discussed herein, as illustrated, for example, in FIGS. 2A through 2D of the present application. In particular, FIGS. 2A through 2D illustrate images under conditions of similar perfusion. FIGS. 2A and 2B illustrate MSPV tissue perfusion). As illustrated, a subject holding their breath for greater than 50 second produced a drop in $SpO_2$ from 98 percent to 91 percent. FIGS. 2C and 2D illustrate $SpO_2$ images and show a 9 percent drop in intensity within the region of interest (ROI—rectangle in $SpO_2$ images).

As discussed in, for example, commonly assigned U.S. patent application Ser. Nos. 13/819,817; 13/833,862; and Ser. No. 15/054,830, imaging optimization may include quantifying the light energy-tissue interaction parameters and MSPV across a range of near-infrared (NIR) wavelengths. These documents are hereby incorporated herein by reference as set forth in their entirety. Referring now to FIGS. 3A through 3C, a series of images illustrating flow data resulting from experimentation in accordance with some embodiments of the present inventive concept will be discussed. The experiments addressed whether existing MSPV illumination configuration (partially coherent 450 nm blue laser and a highly coherent 785 nm red laser) was optimal and whether a depth of detection equal to a depth of penetration is accurate. Using a custom optical phantom setup, with 75 um channels in an imaging array, a non-pulsatile perfusion pump delivered fluid at 0.1-0.2 mm/second consistent with arteriolar/venule flows.

Dilute intralipid was used as a surrogate for blood in experiments discussed with respect to FIGS. 3A through 3C as the micelles mimic the scattering effect of the red cells. Each image is normalized to a specific (wavelength) baseline, and the rest of the images in that row (A, B, C) show relative perfusion across the wavelengths compared to that normalization. In FIG. 3A, each image is normalized to its own baseline, and then by histogram matching to the 730 nm baseline (FIG. 3B), and to the 808 baseline in FIG. 3C.

Carefully controlled coherent laser illumination energy across the FOV for each red NIR illumination that was tested, at 690 nm, 705 nm, 730 nm, 785 nm, 808 nm and 830 nm wavelengths as shown in FIGS. 3A through 3C. FIGS. 3A through 3A illustrate the flow data in the phantom at the same time point in the 2 second, fixed flow and standard illumination energy across the 6 wavelengths. These results illustrate that the 785 nm images have the greatest fidelity, clarity and consistency of flow visualization. Thus, the original configuration selected for MSPV empirically was confirmed to be the optimal red NIR wavelength for MSPV imaging.

Figure 4:
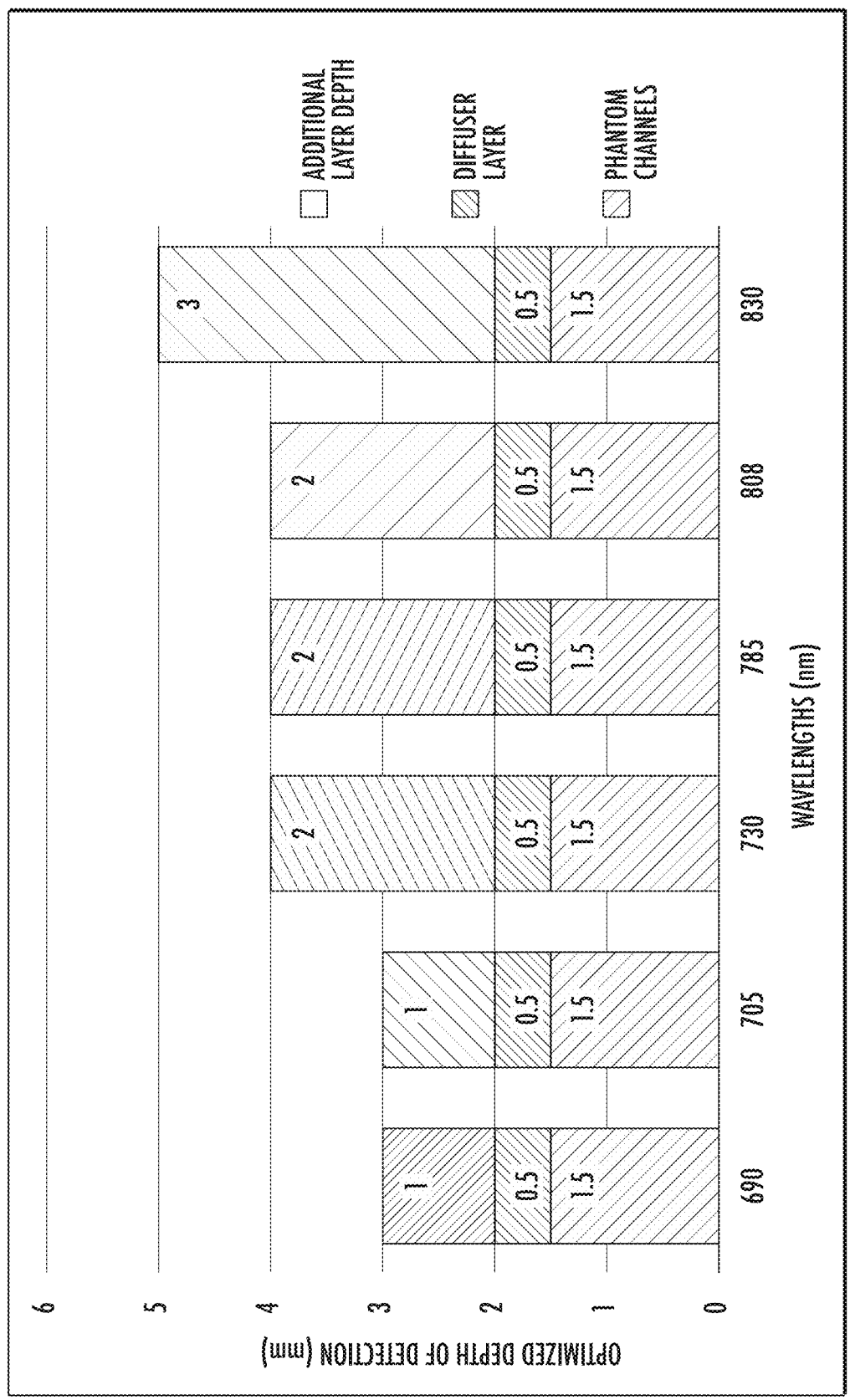
FIG. 4 is a graph illustrating optimized depth of detection (mm) versus wavelengths (nm) in accordance with some embodiments of the present inventive concept.

The optimized depth of detection was determined by using the phantom array with MSPV perfusion as the target (depth of 1.5 mm), with placement of additional 0.5 mm PDMS (polydimethyl siloxane) layers until the optimal phantom target began to lose clarity. A graph of optimized depth of detection (mm) versus wavelengths (in nm) is illustrated in FIG. 4. As illustrated, at 785 nm, the optimal depth was 4.0 mm and extended to 5 mm before image recognition began to be lost. Thus, MSPV can be used to image blood flow distribution physiology in tissues up to a depth of 4 to 5 mm.

Monitoring accuracy of PSPs derived from the imaging metadata has been tested in a clinical study of healthy volunteers in accordance with various embodiments discussed herein. Twenty subjects have been studied. The results of these tests are discussed herein below.

(1) Derivation of relative PSP data: As discussed above, because the MSPV imaging captures the true dynamic nature of blood flow distribution, the physiologic "drivers" for that flow/perfusion are embedded in the metadata of the imaging. The PSPs are derived from the imaging metadata as follows. Raw imaging data from one or more illumination wavelengths are sampled to produce individual laser speckle contrast images, representing the standard deviation/mean/ pixel across all pixels in the FOV. Using a moving window, these contrast images are averaged to produce a laser speckle contrast (LSC) image with is the average SD/mean/pixel for the FOV.

These LSC data illustrate the frequency domain over time of the pixel variation, and represent an intermediate metadata analytical step termed "metaKG." MetaKG indicates a generic physiologic signal derived from the metadata of the MSPV imaging; it describes metadata attributes at each pixel at every frame of the imaging video.

The term mean iKG, a specific subset of metaKG, represents the average density of all LSCI images sampled, where density is equivalent to numerical value/pixel of the LSC image. Isolating and calculating the density of all LSCI images sampled at the systolic peaks of the LSC image results in a systolic iKG, also a subset of metaKG. The iKG values vary inversely with MSPV perfusion, and with BP parameters.

Figure 5A:
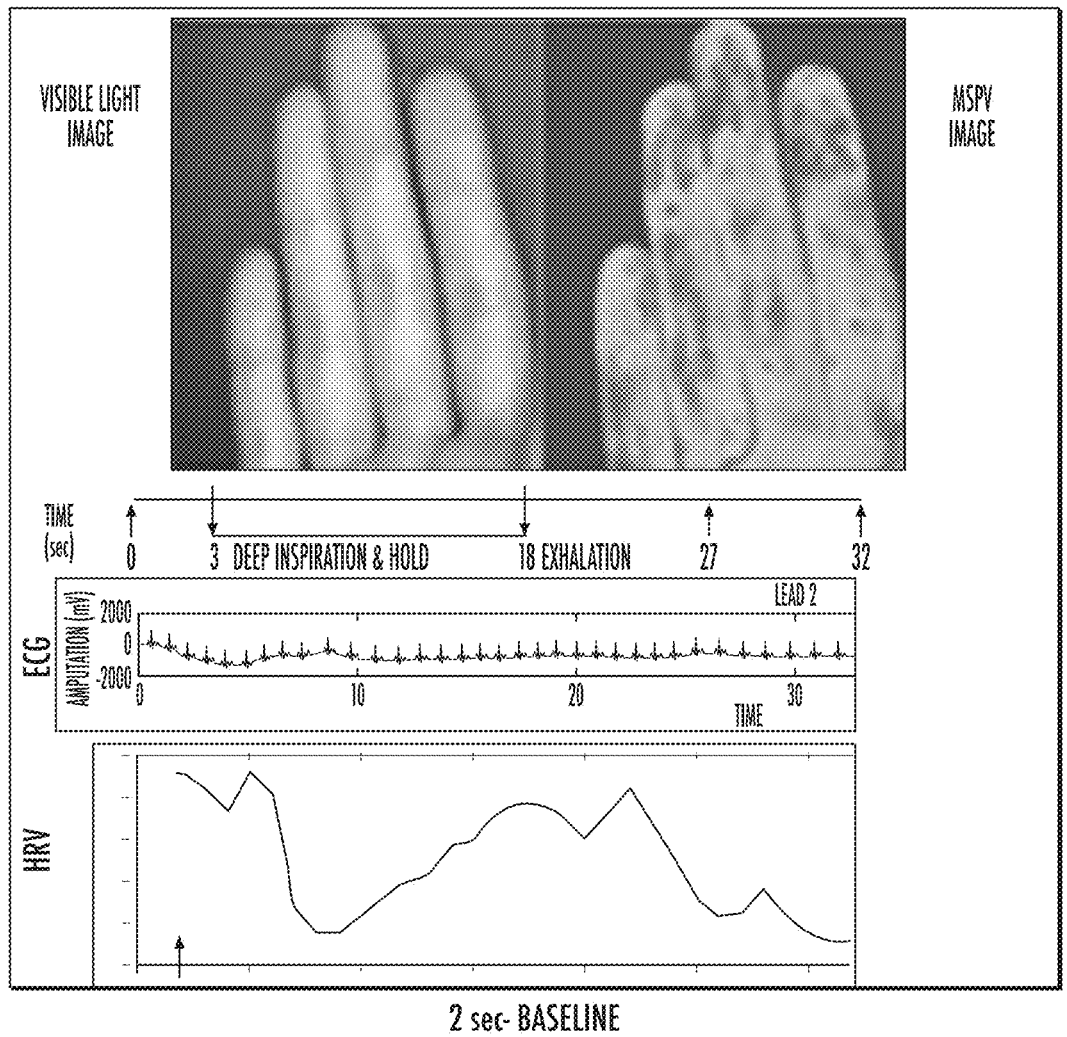
FIGS. 5A through 5C are a series of still images at a 2-second baseline, a 12-second deep inspiration and hold, and a 23 second post exhalation, respectively, in accordance with some embodiments of the present inventive concept.
Figure 5B:
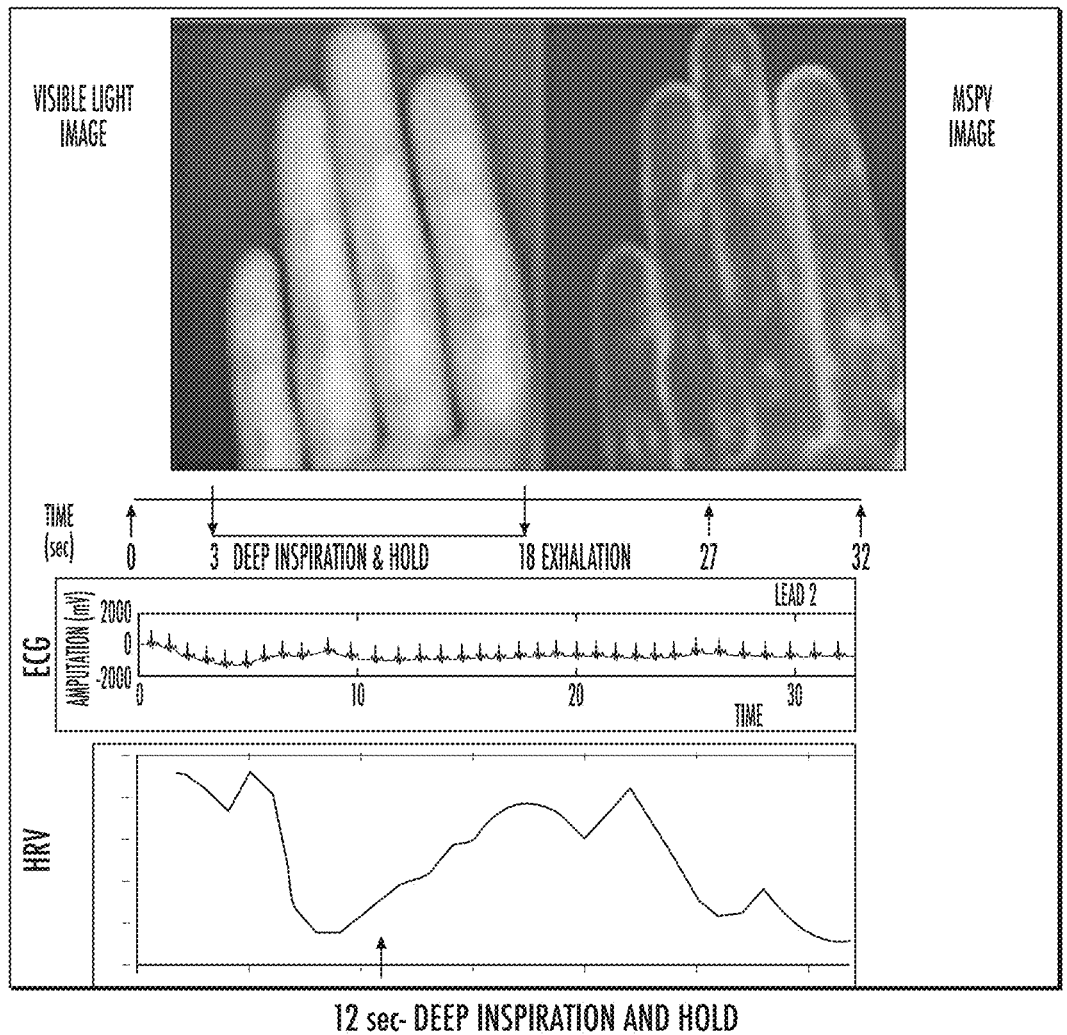
Figure 5C:
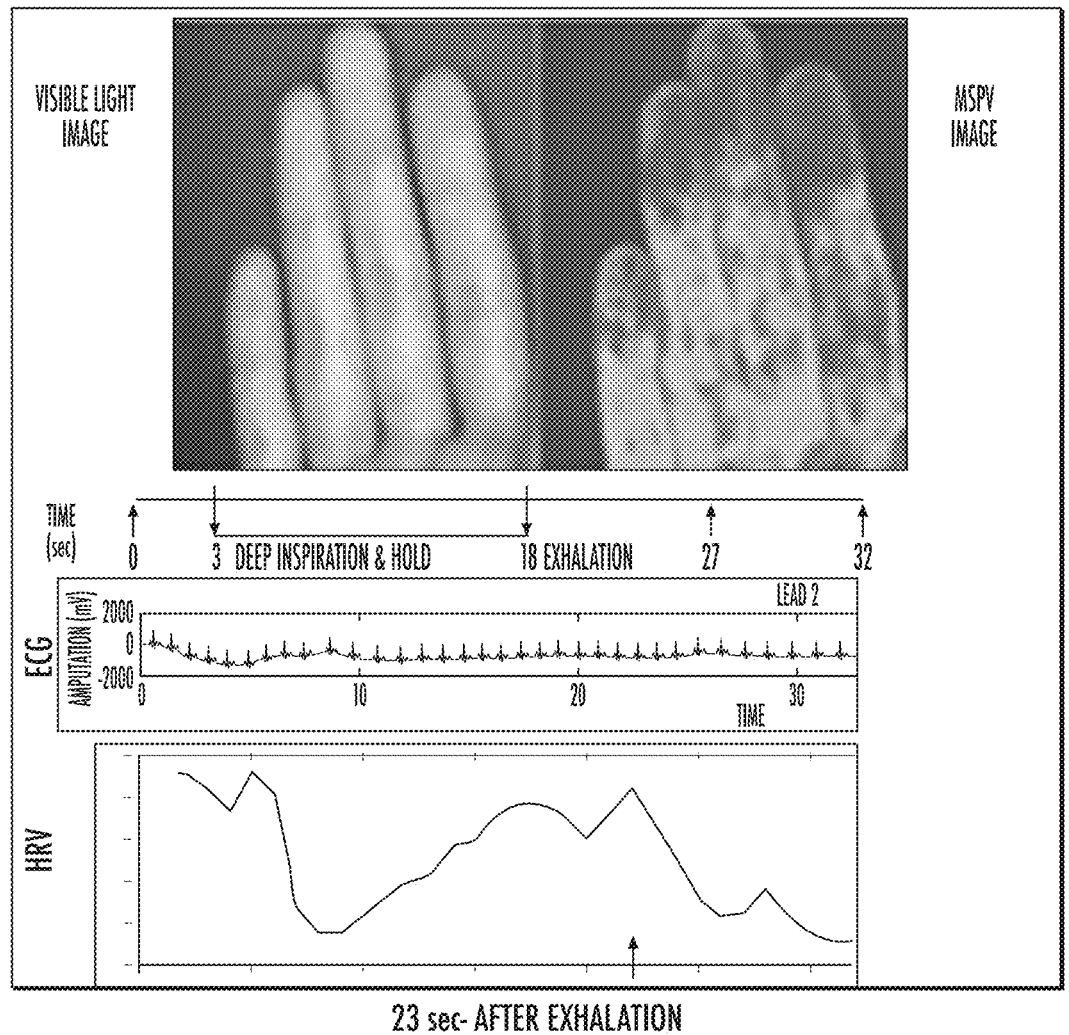

It will be understood that MSPV and the PSP derivative data are relative and not absolute diagnostic values. MSPV captures the speckling pattern of the red blood cells in the vessels and tissues, and determines velocities of flow. Referring to FIGS. 5A through 5C, a series of still images at a 2-second baseline, a 12-second deep inspiration and hold, and a 23 second post exhalation, respectively, in accordance with some embodiments of the present inventive concept will be discussed. In the L panel illustrated in FIGS. 5A through 5C, the MSPV image shows normal relative flow to the digits: normal higher flow to the fingertips, less along the body of the digits due to the lack of pressure and tactile sensors on this part of the digit. The series of images in FIGS. 5A through 5C illustrate a 2 second baseline (5A), a 12-second-deep inspiration (5B), and 23 second exhalation (5C) still images. HRV refers to heart rate variability and ECG refers to electrocardiogram. MSPV visualizes dynamic physiologic changes in real-time.

(2) Relative dynamic fidelity: Testing was performed to assess the ability of the MSPV to detect subtle, normal physiologic changes in perfusion as a result of these maneuvers. The subjects performed a series of physiologic maneuvers (stepwise occlusion of inflow, isometric exercise, Valsalva maneuver, deep inspiration and hold, reperfusion from different inflow levels of occlusion), while MSPV was used to visualize flow changes in the right hand (FIGS. 5A through 5C). FIGS. 5A through 5C illustrates changes to palmar perfusion during a deep inspiration and hold (for 18 seconds), then exhale physiologic maneuver. With exhalation and exaggerated blood flow return to the heart over the subsequent cardiac cycles, there is transient increased perfusion to the hand (at 23 seconds—FIG. 5C). But all these flow velocities are relative to each other in that FOV across the entire imaging sequence, so these three still images are directly comparable.

Figure 6:
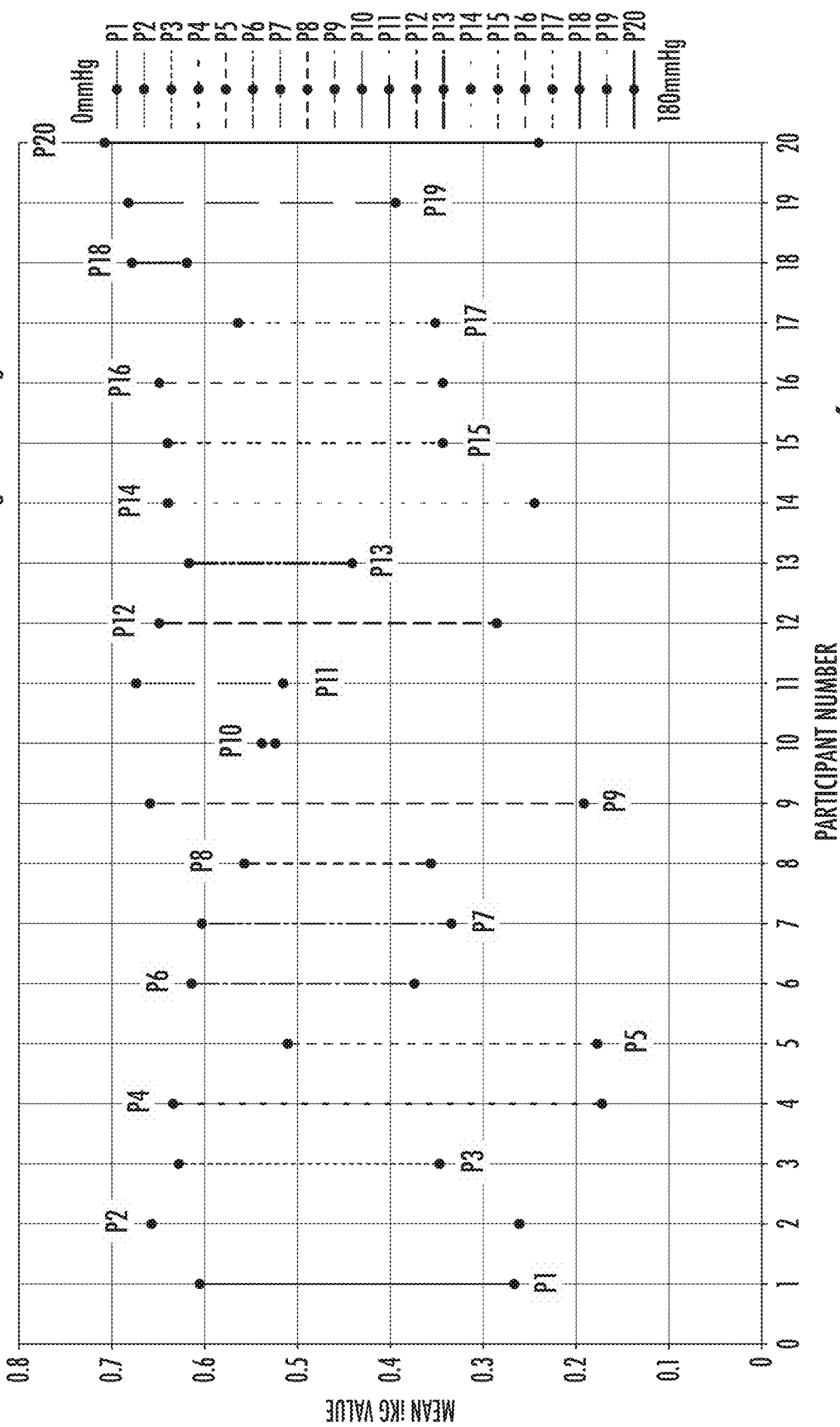
FIG. 6 is a line graph of participant number (one of twenty volunteers) versus mean iKG value associated with imaging a right hand of the participant in accordance with some embodiments of the present inventive concept.

(3) Blood Pressure, HR Correlation: the relative ankle-to-brachial systolic threshold pressure ratio produced in the cABI study is also produced with MSPVO$_2$-ABI in accordance with some embodiments of the present inventive concept. First, the range of mean iKG values at different brachial occlusion pressures at baseline 0 mmHg and every 20 mmHg from 60-180 mmHg was documented across 20 subjects represent in a line graph of FIG. 6. Thus, the first signal of flow after the threshold of occlusion produced by the BP cuff appears to be detectable with MSPV over the physiologic range of BPs (analogous to the doppler signal in cABI). As a "control" measurement, the mean iKG for heart rate was compared to the EKG-determined heart rate. There was a significant range of iKG change over this BP occlusion range that varied directly with perfusion. Second, the mean iKG value for each frame of the video documenting the perfusion change after 25 seconds of brachial occlusion at three different levels (120, 140 and 160 mmHg) tracks the differences in the hyperemic responses upon reperfusion illustrated in the graph of FIG. 7. Due to the gray scale of the figure, note that the lowest curve in frames 1500-2500 (iKG=~0.22) becomes the highest curve (iKG=0.75) in frames 2600-3400 with reperfusion. Third, the baseline analog BP determinations for 10 patients each at 6 conditions of baseline resting state were compared for measurement stability and reproducibility vs. the mean iKG values determined from the imaging. The tightness of fit around the mean (±2 SD) was much better with the iKG determinations than the analog BP measurements taken from each subject under the same conditions with the same automatic device and by the same technician for these 10 of 20 subjects analyzed thus far.

Figure 7:
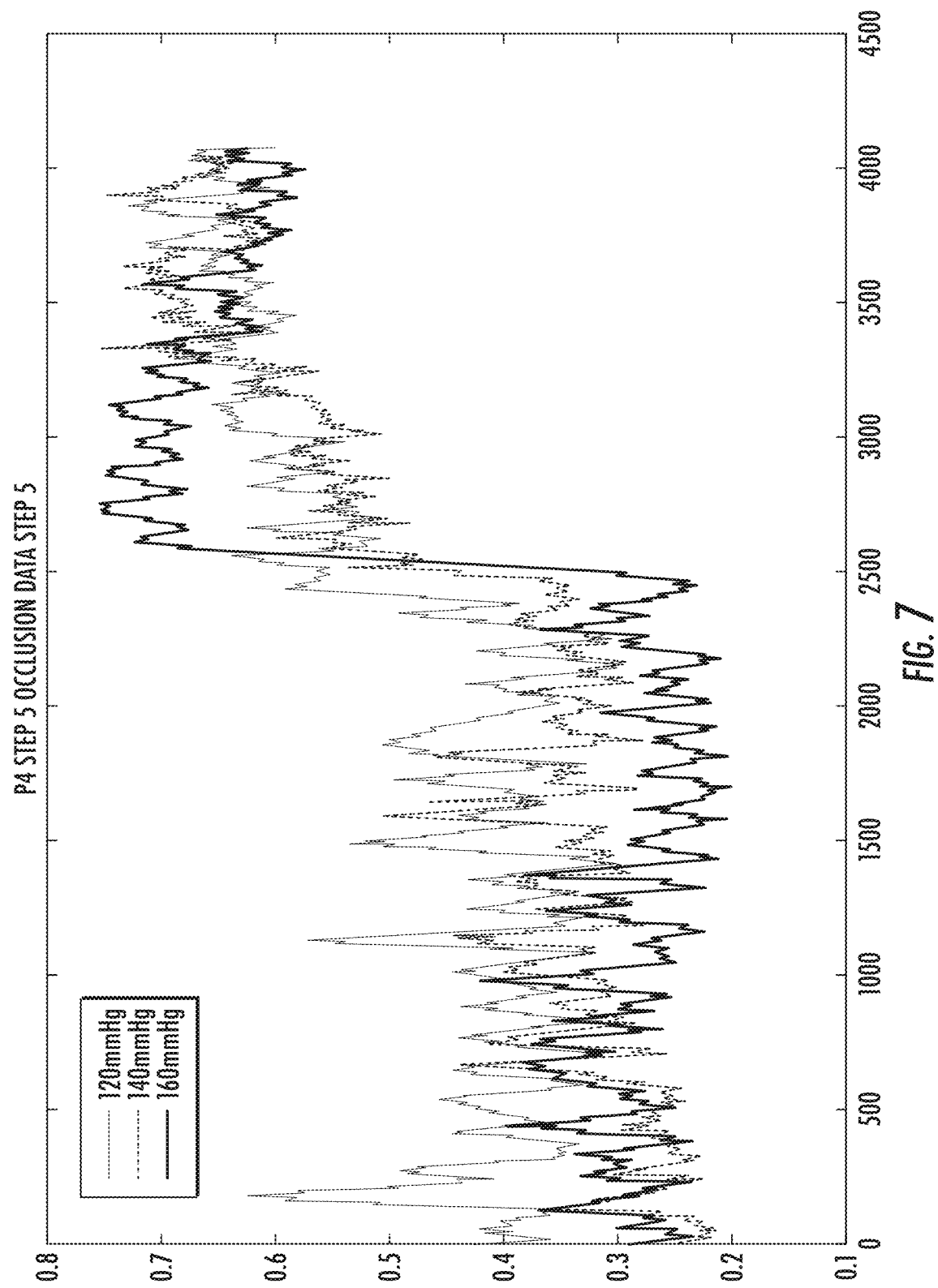
FIG. 7 is a graph illustrating mean iKG (ordinate) at each frame from a 25-second imaging video (abscissa) in accordance with some embodiments of the present inventive concept.

To summarize, for each of the 20 volunteers (P1-P20 of FIG. 6), the palmar surface of the right hand was imaged for 5 seconds at each of 0, 60, 80, 100, 120, 140, 160, and 180 mmHg. The mean iKG from each of the baseline and 180 mmHg values are plotted on the ordinate. Three volunteers had outlier data: P10 had a malfunctioning cuff, and no occlusion was produced (investigators were blinded to the imaging during data acquisition); P11 and P18 had excessive hand movement during the 180 mmHg imaging acquisition. FIG. 7 illustrates mean iKG (ordinate) at each frame from a 25-second imaging video (abscissa) in accordance with some embodiments of the present inventive concept. As shown, the reperfusion response from three different occlusion pressures (mmHg; 120=(solid line) blue, 140=(dotted line) red, 160=(dashed line) green). The hyperemic response is greatest from the highest occlusion pressure.

Figure 8A:
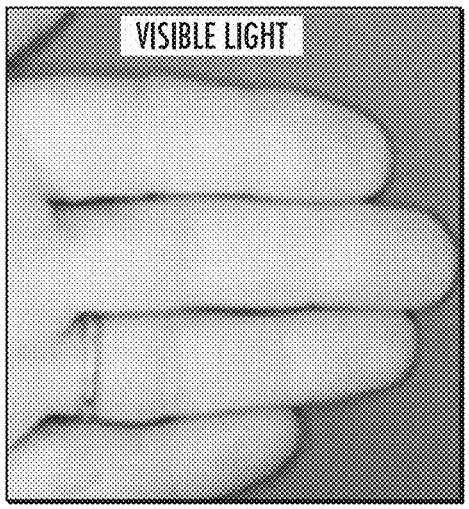
FIGS. 8A and 8B are still images of a left hand (8A and 8B) and left foot (8C and 8D) of a subject from a video illustrating various aspects of the present inventive concept.
Figure 8B:
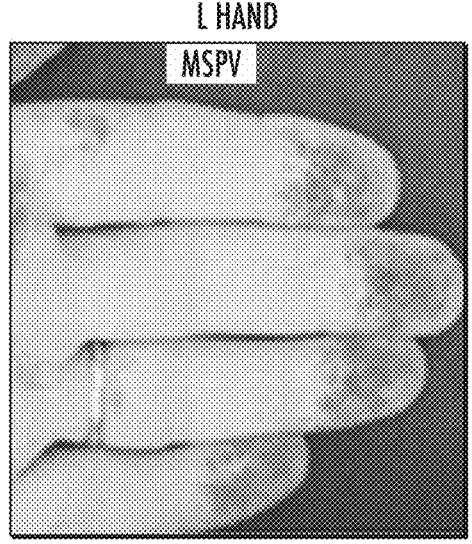
Figure 8C:
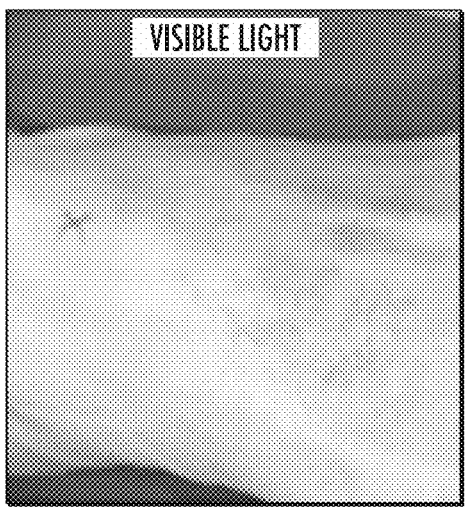
Figure 8D:
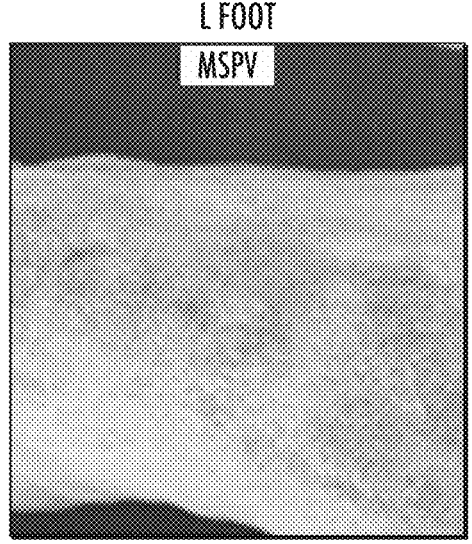

Embodiments of the present inventive concept provide that cABI-type hemodynamic data and these end-organ tissue- and perfusion-related physiologic data can be captured and integrated together in real-time using this platform. FIGS. 8A through 8C illustrate using an iCertainty device, still images from a video. The palmar surface of the left hand (FIGS. 8A and 8B) and the top of the right foot (*dorsalis* pedis distribution) (FIGS. 8C and 8D) were imaged sequentially, followed by the analog systolic BP in a normal subject. The ratios are equivalent.

Figure 9:
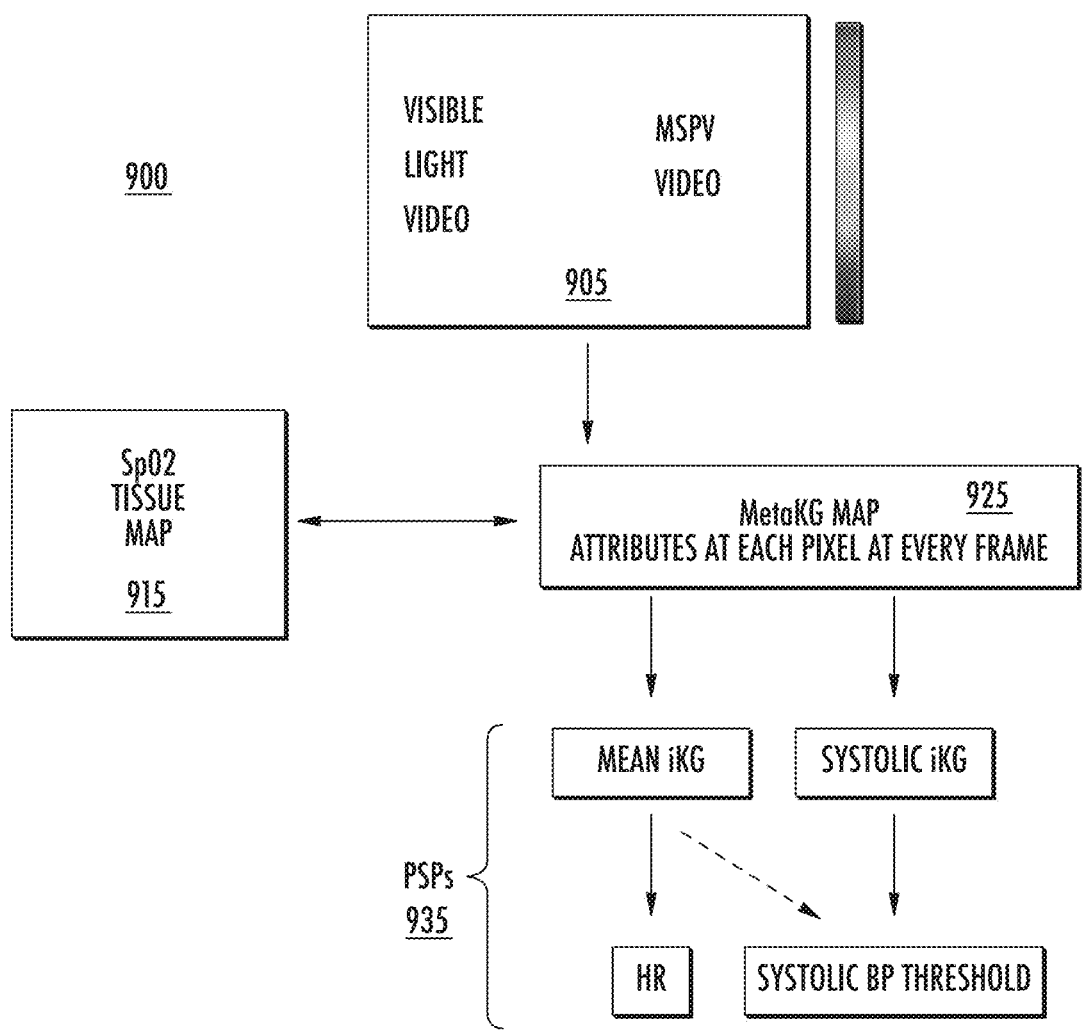
FIG. 9 is a block diagram illustrating integration MSPV, $SpO_2$ tissue mapping, metaKG mapping and physiologic status parameters (PSP) in accordance with some embodiments of the present inventive concept.

Some embodiments of the present inventive concept provide integration of MSPV perfusion, metaKG physiologic parameters, and SpO$_2$+[Hgb] measurement and quantification in real-time. A block diagram illustrating the integration of the various systems is illustrated in FIG. 9. As illustrated, the system 900 may include MSPV 905, SpO$_2$ 915, metaKG 925 and PSP 935 components. In particular, the system includes the imaging hardware (MSPV and SpO$_2$), the imaging software (data acquisition, management), and the combined analyses of the MSPVO$_2$-ABI approach in a benchtop optical physics phantom model. FIG. 9 is provided as an example only and embodiments should not be limited to the structure illustrated therein. SpO$_2$ data integration is at the metaKG level; both are maps (not videos); correlating the SpO$_2$ with the relative quantitative MSPV perfusion data is inexact, even with a color bar (shown in gray scale). The metaKG and iKG analyses, the SpO$_2$ analyses, and the MSPV analyses may run in parallel. The display (FIG. 10) may illustrate the MSPV video, along with the SpO$_2$ tissue map and the PSP data displays.

Experiments may be performed to illustrate results achieved in accordance with embodiments of the present inventive concept. For example, two (2) custom built PDMS optical phantoms, each with a different diameter channel (5 mm, 2.5 mm), having flow/perfusion assessed by MSPV imaging. A pulsatile microperfusion pump delivering fluid at the same flow rate will be used to mimic heart rate, and the resistance difference between the two channels will mimic differences in BP. This will provide the imaging metadata substrate necessary to generate metaKG and PSP data. The optimized validated solution and design for $SpO_2$ determination is incorporated into the MSPV system. At the distal end of each channel, a non-transmissive $SpO_2$ light emitting diode (LED) may measure the channel fluid oxygen content.

To produce speckle essentially the same as from RBCs in blood, a 0.9 percent intralipid solution may be used. To tackle the difficult issue of mimicking hypoxemia and hypoxia, the veterinary blood substitute Oxyglobin ($HbO^2$ Therapeutics, Souderton, Pa.) will be added at differing concentrations to the diluent, to produce fluid oxygen levels of 0%, 50 percent, 80 percent, 90 percent, 95 percent and 98 percent while keeping the fixed number of scatters in the same total fixed volume. Oxyglobin is stable at room temperature, is a white milky fluid like intralipid, and won't affect the MSPV imaging fidelity when included as a diluent.

The development MATLAB version of the MSPV software may be modified to (serially) acquire and then analyze MSPV and $SpO_2$ imaging data (both MSPV illumination and $SpO_2$ illumination cannot be active at the same time). Algorithms for determining $SpO_2$ and for generation of the MetaKG and iKG results are included into the MSPV architecture, including (simultaneous) management of real-time image and analysis data captured from two OHUs.

Each phantom "run" may be only 3-4 seconds in duration. Each phantom study tests hardware and software modifications at each oxygen level as needed until all issues (hardware aspects (illumination, focal length, imaging acquisition timing, FOV); data capture; illumination sequence; real-time acquisition; parallel analysis; display considerations; software control of electronics and device components) are resolved. Finally, a new fully functional MATLAB version of this integrated $MSPVO_2$-ABI software may be tested using the phantom in a final series of tests at each oxygen level.

Repeated measures studies may be performed to optimize the reliable collection of these data in real-time. Once the final hardware and software determinations are made, a minimum of six (6) determinations at each of the oxygen levels will be used. At each of these studies, confirmation of the: 1) consistency of MSPV flow/perfusion; 2) the generation and consistency of the metaKG and PSP determination (HR, BP); 3) Bland-Altman plots will be used to test the consistency and differentiation of the $MSPVO_2$-ABI oxygen saturation levels vs. the peripheral oxygen sensor data and the calculated O2 concentration in the perfusion fluid.

Pre-clinical and clinical $MSPVO_2$-ABI prototypes may be designed, engineered, built, tested and validated. FIG. 10 is a block diagram illustrating various aspects of the system in accordance with embodiments discussed herein. FIG. 10 is a schematic of a medical system in accordance with embodiments discussed herein.

The system can include Clinical Device User Requirements (UR). This can include clinical data to be captured, user-patient interface, utility and durability requirements, device communication requirements, and operational parameters for a Clinic environment.

Embodiments of the present inventive concept may have various form factors without departing from the scope of the present inventive concept.

As discussed above, a MATLAB-based research application can be converted into a C++ clinical software graphical user interface (GUI) and operating system platform. For embodiments of the $MSPVO_2$-ABI system discussed herein, a software module may be configured to 1) simultaneously control, data collection and data analysis from two (2) OHUs; 2) incorporate of real-time $SpO_2$ acquisition and analysis and metaKG PSPs into the existing MSPV architecture based on the schema in FIG. 8; 3) create a modified analysis display incorporating this new additional information along with the MSPV analysis; 4) modify of the clinical data variables captured by the $MSPVO_2$-ABI device on all patients; and 5) make a final determination of the data repository and communication parameters for the device. Related clinical devices may be configured to upload clinical, imaging, analysis and imaging acquisition parameter data to a web-based secure HIPAA-compliant data repository.

Some embodiments of the present inventive concept can be tested using a well-established experimental porcine model. The porcine model may be used for MSPV and $SpO_2$ imaging acquisition and device development.

In an anesthetized, monitored and ventilated 50-60 kg female porcine model, an extensive bilateral femoral artery cut down may be performed. With the left (L) and right (R) common femoral artery and branches isolated, fluid-filled catheters will be introduced to monitor distal femoral artery pressure. Each OHU (FIG. 10) will image a femoral artery cutdown FOV, including the artery and surrounding muscle, soft tissue and skin in equivalent Fields of View. The distal left and right hindlimb skin will be monitored with pulse oximetry.

BP Correlation: The proximal R common femoral artery will be temporarily narrowed (25%, 50% and 75% occlusion) for 4 minutes before simultaneous imaging, to mimic the setting of brachial vs. ankle pressure discordance as seen in PAD patients. The $MSPVO_2$ of the skin and tissues will be captured as well, and the metaKG will be analyzed using mean iKG and systolic iKG determinations. Ten (10) sets of measurements (15 second imaging duration each) at each occlusion stage in 5 animal experiments is anticipated.

Hypoxemia and Hypoxia: It is expected that reducing the femoral artery inflow will not produce flow-induced hypoxemia in 4 minutes. Once the iKG data are generated, this protocol will be modified with a 10- or 15-minute 75% narrowing, with a 75% reduction in the ventilatory rate over 5 minutes at 75% narrowing, and with a 30 min interval 75% narrowing. It is anticipated that this last maneuver will cross the line from hypoxemia to hypoxia. Five (5) sets of measurements at each condition, with full recovery in between, in 5 experiments, as above.

The mean iKG and systolic iKG determinations will be correlated with the HR and mean and systolic peak transduced BP signals using Bland-Altman plots. Correlation coefficients will be determined for HR, BP and $SpO_2$ (average of skin in FOV). Based upon the transduced BP recordings, we will determine if possible whether the mean iKG or the systolic iKG analysis is more suited for ABI determination; this is in preparation for the direct comparison. Differences between the L (control) and R hindlimb perfusion, oxygen saturation and pressure during these inflow occlusions and ventilatory maneuvers will be determined.

As discussed above, some embodiments provide a new test, $MSPVO_2$-ABI. Some embodiments of the present inventive concept may involve clinical studies to further develop the test discussed herein. It will be understood that these studies may provide different or updated devices, methods and the like. However, the basic concept remains the same as discussed herein. MSPVO$_2$-ABI may not replace cABI testing; rather, there is a potential subset of PAD patients in whom MSPVO$_2$-ABI might prove useful, where cABI has limitations. Also, the real-time data generated by the MSPVO$_2$-ABI device might give new and important insight into PAD evaluation, where combining the anatomy of perfusion with real-time perfusion physiology data might prove beneficial.

In some embodiments, the subjects (patient population) may include those who meet the clinical and symptomatic criteria for cABI testing. In particular, patients where PAD is not indicated as a screening test in asymptomatic patients and cABI is the initial test for referred patients with symptoms, and occasionally in patients with complicating factors who are asymptomatic. Importantly, each Vascular Clinic's patient demographics should be dissimilar, thus that they cover the broad range of patients with early- and mid-stage symptomatic PAD. These demographic differences include, but are not limited to, race, gender, and some but not all major cardiovascular risk factors. The more diverse the patient pool, the more relevant the studies will be.

The protocol for the testing may take many forms without departing from the scope of the present inventive concept. The MSPVO$_2$-ABI study may be added to a cABI visit and performed immediately after the ABI study is completed and documented. The patient will remain supine at rest, and the MSPVO$_2$-ABI device may be activated. Key clinical patient demographic, clinical and PAD disease variables are entered into device software, and the imaging window appears. The device is positioned for ipsilateral simultaneous collection of hand perfusion and ankle perfusion, focusing on either the posterior tibial or dorsalis pedal arteries. The imaging activation sequence is 10-20 seconds in some embodiments. Both distal arteries are evaluated using, in some embodiments, a total of two imaging activation sequences/side. The other side may then be imaged in a similar fashion. If the cABI is a rest/exercise test, then the MSPVO$_2$-ABI study will be performed in the same manner.

Data may be collected at all stages and then stored and analyzed. In some embodiments, all study data may be captured and entered into the encrypted hard drive on the MSPVO$_2$-ABI device, which meets all standards for HIPAA compliance as well as other privacy rules. No other paper data collection may be needed outside of the consent form. Once trained, it is anticipated that, for example, a Nurse Coordinator or Ultrasound technician, may complete the MSPVO$_2$-ABI Testing Protocol in 10 min or less.

The content of the data may vary. Variables captured in the software may include, for example, name, date of birth, gender, date of service, Attending Physician, cardiovascular risk factors, PAD risk factors, prior cardiovascular and cerebrovascular history including prior procedures, and categories of cardiovascular medicines if any medication is being taken. A screen for entry of the current cABI data may be present. Also, a screen for documenting subsequent testing prescribed by the Attending Physician, and any results from that testing, is present, as is a screen for any subsequent interventions. The current MSPV iCertainty software is configured to collect similar data online. Finally, free-text entry may permit direct, real-time feedback from the user and patient about the test, the experience, and the device functionality.

The two ratio measurements for each ipsilateral side will be correlated at the individual patient level to test for agreement between the two techniques (MSPVO$_2$-ABI and cABI). To test the statistical similarity between the MSPV-SpO$_2$ and analog BP data, a modified Koch's test of equivalence for a mixed-effects repeated measures model will be used to determine the statistical similarity between MSPV+SpO$_2$ ($\xi$1) and CIM ($\xi$2) parameter estimates. Given the decision criteria D1: $-\Delta \leq \xi 1 - \xi 2 + \Delta$, where $\Delta=10$, the estimates are deemed equivalent (accept D1) if the 95% confidence interval (CI) for $\xi$1-$\xi$2 falls within the A equivalence region).

The incidence of major cardiovascular risk factors in each population will be correlated with the MSPV perfusion and SpO$_2$ data empirically on a per patient basis. Calculation of sensitivity and specificity of the cABI and MSPSVO2-ABI testing in pooled data with specific risk factors will be compared to the results of the overall tests across the entire population.

It is possible, but unlikely, that the correlations between BP measurement and iKG is less consistent in the ABI setting. The opportunity to examine both mean iKG and systolic iKG analyses will be important in this context.

The limitations of cABI in asymptomatic patients creates an opportunity for novel solutions using novel technologies. Some embodiments of the present inventive concept may provide reliable, new, and integrated data for the initial evaluation in PAD patients with asymptomatic/complex clinical presentations and may address an important and compelling healthcare need.

As discussed above, the development of the MSPVO2-ABI technology solution to enable the efficient evaluation of the 50% of PAD patients who are asymptomatic will address an important and compelling healthcare need with a reliable, robust, safe and simple technology form factor. Embodiments of the present inventive concept would not be intended to replace existing technology, but augment it with new, important data directly applicable to the clinical context in need of a solution. Some embodiments have the potential to produce new data on the physiology context of PAD.

Accurate, real-time assessment of tissue integrity is a critical need across multiple medical care delivery settings, from open surgical procedures to outpatient diabetic foot care. The common thread linking these care delivery settings is tissue integrity status (TIS)—where on the spectrum from normal TIS to damaged and unrecoverable TIS do the encountered tissues fall. Surgeons are forced to guess about the adequacy of blood flow in tissues across all procedures, and recent data document that they guess incorrectly about 15 percent of the time. Wound care therapies are prescribed on a trial and error basis because the basic pathophysiologic processes of inflammation and healing cannot be reliably differentiated. Approximately 40% of patients with diabetes and peripheral arterial disease will end up with a tissue amputation procedure because the relative pathophysiological interaction of microvascular vs. arterial disease cannot be readily determined.

TIS is determined by 1) blood flow distribution (flow in vessels and perfusion to the tissues); 2) oxygen delivery, unloading, and interaction with the tissues; and 3) the influence of local and/or systemic disease co-morbidities in the tissues in question that affect #1 and #2. Pathophysiologically, this triad combines ischemia, hypoxemia, and hypoxia together in a continuum and emphasizes their real-time clinical interdependence in exerting effects on tissue integrity. Blood pumped through the circulatory system by the heart distributes O$_2$ to each of the $10^{14}$ cells in the human body. O$_2$ is essential for normal aerobic metabolism, and is critical to survival because it functions ultimately as the final electron acceptor in the mitochondrial respiratory chain, which provides a highly efficient means to harvest energy captured in the chemical bonds of glucose and fatty acids. Hypoxia is a state of low oxygen content and partial pressure in the cell. Each cell in the body can sense the $O_2$ concentration and respond to hypoxia by increasing the activity of hypoxia-inducible factor 1 (HIF-1), which functions as a master regulator of $O_2$ homeostasis by controlling both $O_2$ delivery and $O_2$ utilization.

Across different cell types, metabolic demands, and abilities to adapt to hypoxia, the cellular response to various levels of tissue hypoxia can vary from substantial adaptation to cell death. Tissue hypoxia can be caused by one of three abnormalities: hypoxemia (low blood oxygen content and pressure), impaired oxygen delivery to tissues (altered blood flow distribution), and impaired tissue oxygen extraction/utilization. Thus, an ideal technology to assess tissue integrity should quantify blood flow distribution, oxygen saturation and hemoglobin, and be able to characterize additional disease-related factors that can impact the integrity of critical tissues, all in true real-time.

Hypoxemia is defined as a low oxygen content in arterial blood, and can result from altered inspired $FiO_2$ (altitude), ventilation/perfusion mismatch in the alveolar spaces, normal or abnormal hemoglobin uptake of $O_2$ in the alveoli, and the amount of hemoglobin in the blood and abnormal binding properties. $SpO_2$ monitoring is closely associated with hypoxemia, where arterial oxygen tension is below "normal" values, but is unassociated with hypoxia, which is the failure of oxygenation at the tissue level producing anaerobic metabolism. Hypoxemia and hypoxia can be differentiated in part by simultaneously knowing the perfusion status to the tissues, and/or the oxygen carrying capacity in the blood. A rise in $SpO_2$ from 88 percent to 92 percent increases the oxygen content in the blood by 4%. In contrast, increasing [Hgb] from 8 g/l to 12 g/l increases the oxygen carrying capacity by 33%, and doubling the cardiac output in this situation increases oxygen delivery to tissues by over 60% without any change in $SpO_2$.

Overall, oxygen delivery depends upon two factors: $O_2$ content and cardiac output. Normal tissue oxygen delivery is regulated by region, but in normal tissues is ~1000 ml/min Only 25 percent is extracted by the tissues, however, and normal oxygen consumption is ~250 ml/min. However, disease states can alter this oxygen consumption in tissues. For example, there is a general negative effect of diabetes on HIF-1 activation, thereby decreasing this normal level of oxygen consumption even in the face of normal delivery.

The differentiation between injury and regeneration is also difficult to assess in terms of tissue integrity. With regeneration, increased cell mass and cell number both lead to increased $O_2$ consumption; in the absence of a change in perfusion, hypoxia can occur to interrupt the regeneration process. But tissue regeneration is frequently also accompanied by angiogenesis—the development of new capillaries from existing vessels—in part as a response to the regeneration-induced hypoxia. This regeneration milieu emphasizes the criticality of assessing perfusion, oxygenation, and physiologic status parameters simultaneously in true real-time to assess these complex physiologic and pathophysiologic processes.

For point-of-care monitoring, analysis of MSPV metadata (called iKG) reveals the physiologic drivers of that blood flow distribution. These analyzed metadata are termed Physiologic Status Parameters (PSPs), and include (among others) tissue perfusion (TP), dynamic change in tissue perfusion (DCTP), tissue ischemia (TI), systolic, diastolic and mean blood pressure (BP), heart rate (HR), HR variability (HRV), respiratory rate (RR), relative index of sympathetic tone, and relative index of contractility. This optimized configuration for skin imaging may be used to document in normal healthy participants real-time, subtle physiologic responses (change in BP, HR, perfusion) to normal physiologic maneuvers (deep inspiration, sitting, standing, isometric exercise) evidenced by non-contact imaging of the palmar surface of the hand and determination of the PSP iKG values as illustrated in FIG. 11.

Figure 11:
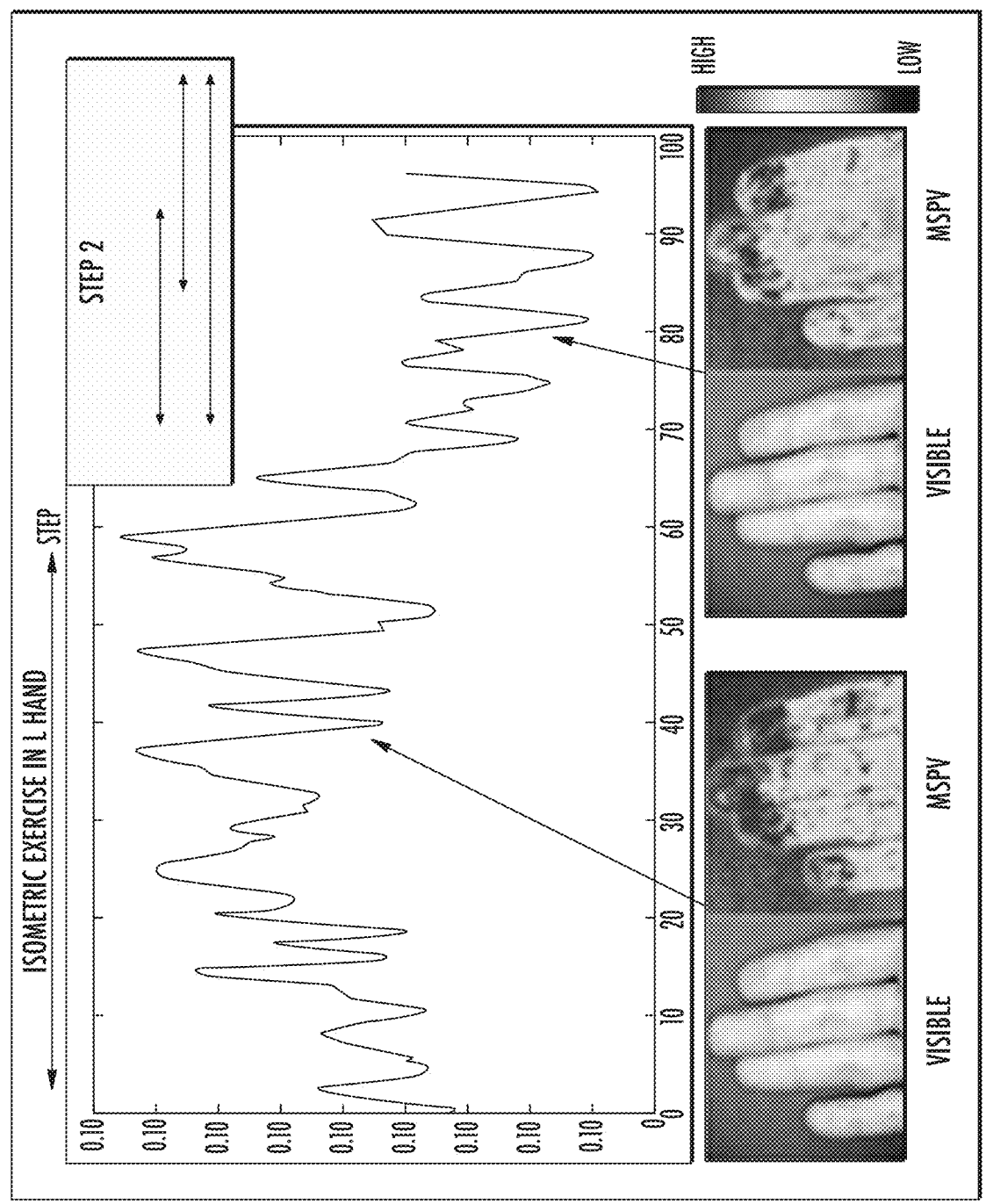
FIG. 11 illustrates a 15-second iKG trace from the metadata of the MSPV imaging of a right hand during and after isometric squeezing of a ball in the left hand, following the Step 2 timing diagram in accordance with some embodiments of the present inventive concept.

FIG. 11 is a 15-second iKG trace from the metadata of the MSPV imaging of the right hand during and after isometric squeezing of a ball in the left hand, following the Step 2 timing diagram. With the left hand exercise, the right hand perfusion is increased, which then goes back to normal perfusion after exercise stops.

Referring now to the flowchart of FIG. 12, a flowchart illustrating processing steps in data integration in accordance with some embodiments of the present inventive concept will be discussed. Methods according to embodiments of the present inventive concept provide an imaging sequence of about 10-12 seconds that provides all the data required to produce: (1) the real-time blood flow distribution visualization in the entire FOV; (2) the peripheral oxygen saturation at the tissue surface level for the entire FOV; and (3) the generated PSP data detailing the actual physiology of blood flow distribution in numeric format for analysis. These data are generated in true "real-time" for the entire FOV through parallel processing of the three individual data streams captured as part of the imaging acquisition. The data results are then re-integrated (video for MSPV, still image for $SpO_2$, graphic description of the numeric PSP data) for display. The MSPV data (and metadata-derived PSP data) are captured as a matrix file; the $SpO_2$ data are captured as an individual value for each pixel in the FOV and as the averaged per pixel deoxyhemoglobin/oxyhemoglobin ratio for the entire FOV.

Figure 12:
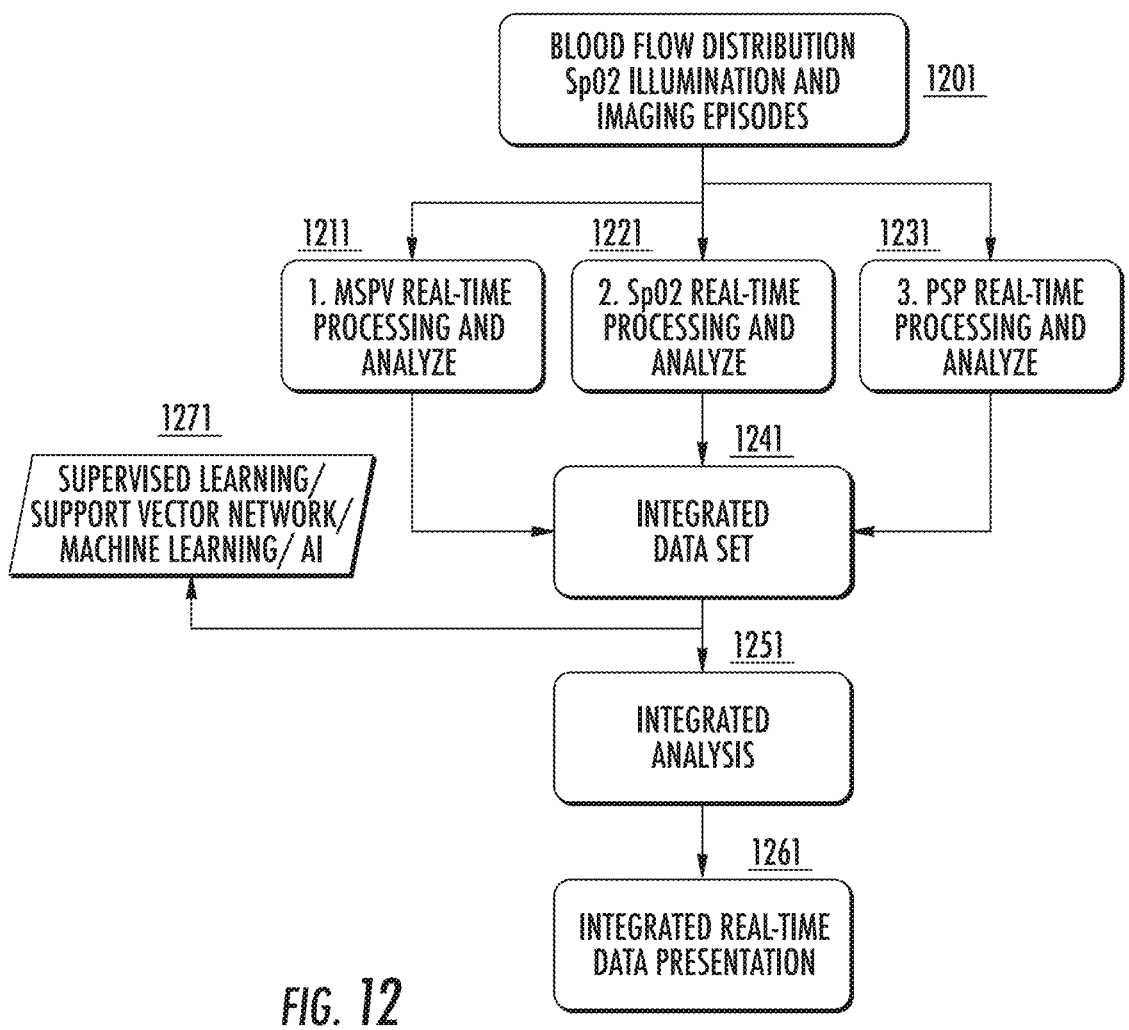
FIG. 12 is a flowchart illustrating data integration in accordance with some embodiments of the present inventive concept.

As illustrated in the flowchart of FIG. 12, operations begin at block 1201 by illuminating the target for blood flow distribution and $SpO_2$ to image the sample. In parallel, operations proceed to blocks 1211, 1221 and 1231 for MSPV, $SpO_2$ and PSP, respectively, real-time processing and analysis. The data set may be integrated (block 1241) and analyzed (1251), then presented to the user (block 1261). It will be understood that at some point in the process this data may be provided to an external source/engine (block 1271) where the data can be analyzed using artificial intelligence (AI) algorithms and the like. In other words, the data can be analyzed using supervised learning, support vector network, machine learning, AI and the like. In some embodiments, algorithms and rules are used by the machines learning to analyze the output of the system and provide various types of information for use in a clinical environment. For example, the data may be used for diagnoses, testing and teaching in some embodiments.

Some embodiments of the present inventive concept provide modules for real-time acquisition and analysis of data as discussed above. These modules provide secure data imported to and/or exported from the network attached storage system. Due laws about privacy, especially in healthcare, aggregate data may be de-identified, and the imaging, $SpO_2$ and PSP data have no patient identifiers in the digital datasets. Each entire imaging episode digital dataset including the MSPV, $SpO_2$ and PSP data in the structure may be labeled for overall data management, i.e. use by the various engines to provide derived data and diagnoses.

In some embodiments, the component values may be classified along a relative clinical continuum. Absolute data values for this classification generally do not exist, so this is an estimation process that continuously undergoes revision as the framework development proceeds. For example, the percentage of blood flow interruption to cause tissue ischemia is variable across tissues, and the hypoxemia 4 hypoxia threshold differs across tissues as well. Furthermore, these pathophysiologic processes occur over time, a factor not included here but which can be assessed using this approach by serial data capture and analyses. Since the MSPV blood flow distribution assessment is relative across the FOV, perfusion abnormalities can be determined by the percentage of relatively abnormal perfusion in the FOV; this same principle can be used for $SpO_2$. The PSP iKG range is from 0.0-1.0, and is a dimensionless value.

Figure 13:
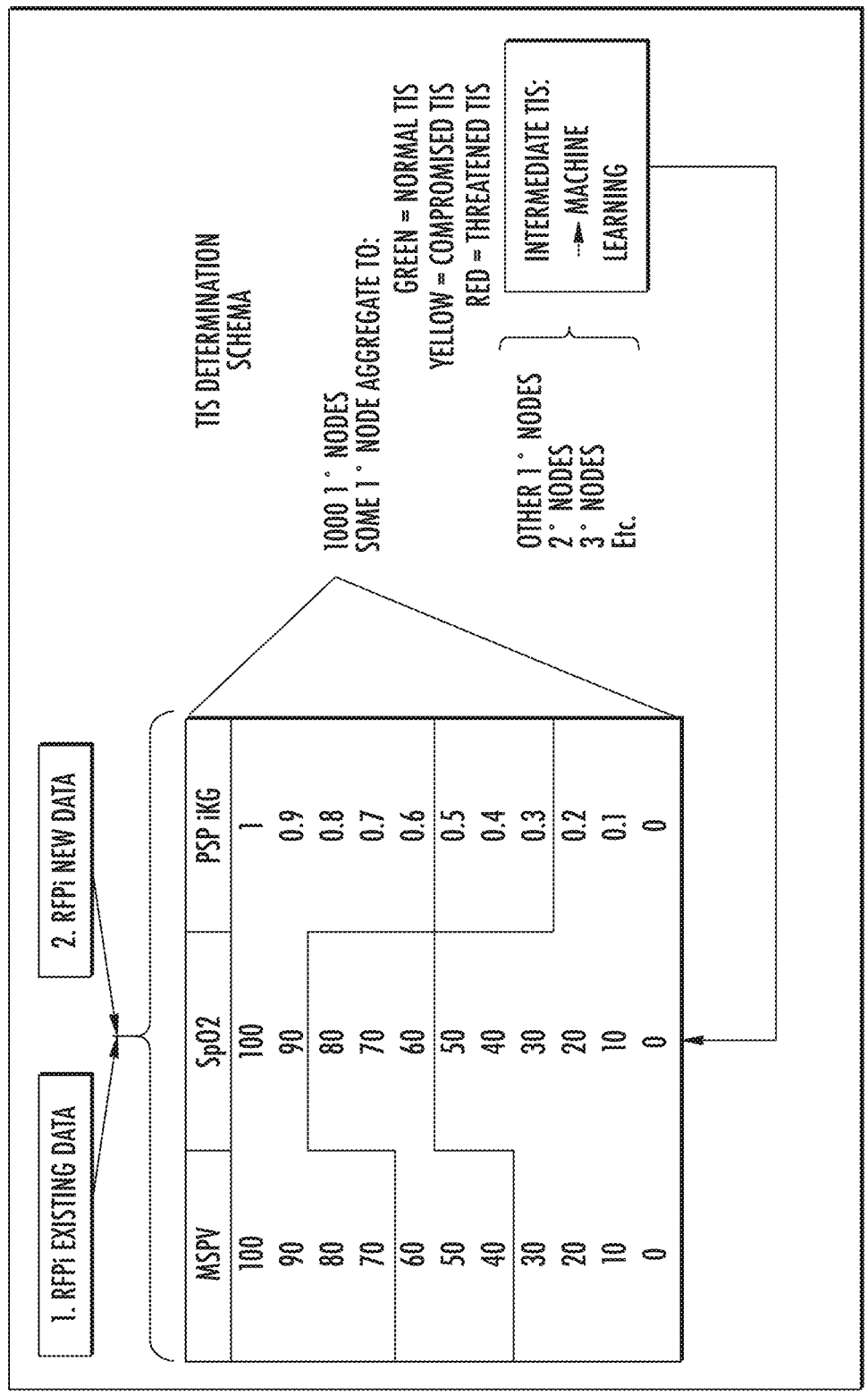
FIG. 13 illustrates an initial classification (green=normal, yellow=compromised, red=threatened) for MSPV, $SpO_2$, and PSP iKG in accordance with some embodiments of the present inventive concept.

FIG. 13 illustrates an example initial classification (green (top box)=normal, yellow (middle box)=compromised, red (lower box)=threatened **if shown in color) for MSPV, $SpO_2$, and PSP iKG. Since FIG. 13 is presented in gray scale, the results are summarized as follows: MSVP: red=0-30; yellow=40-60 and green=70-100; $SpO_2$: red=0-50; yellow=60-80; and green=90-100; and PSP iKG: red=0-0.2; yellow=0.3-0.5 and green=0.6-1.0. These initial thresholds are arbitrary and are provided as examples only and, therefore, may be refined through the feedback and the new experimental and clinical data inputs over time, as shown in FIG. 13.

In some embodiments, to link these results to tissue integrity, a three-dimensional matrices of the individual component values (MSPV, $SpO_2$, PSP iKG) is constructed and then combined component values (MSPV+$SpO_2$+PSP iKG→green, yellow, red). Example frameworks are provided. It will be understood that FIG. 13 is provided for example only and embodiments of the present inventive concept are not limited thereto.

In detail, each matrix may have each component or combined components as a node in the framework, across the continuum from normal tissue integrity (normal MSPV, normal $SpO_2$, normal PSP iKG) to threatened tissue integrity (abnormal perfusion, hypoxia, loss of PSP iKG). In accordance with embodiments discussed herein, these matrices may be further refined using existing and new experimental data as it becomes available.

In some embodiments, the engines may use existing data, data derived from existing data and constantly acquired new data. Existing data may include archived normal and ischemic tissue. This may include data from three large animal experimental preparations; five different tissue types in each preparation. This data may be carefully evaluated every 10-30 minutes along a two-hour ischemic continuum in some embodiments. This existing data visualizes the MSPV imaging spectrum from normal to histologically necrotic tissues.

Furthermore, the existing data may be analyzed using various engines that apply relevant algorithms for testing, diagnostics, teaching and the like. From the archived raw MSPV ischemia imaging metadata, corresponding PSP data may be generated for each timepoint along the tissue ischemia continuum;

Finally, new data may be constantly collected, stored and analyzed. For example, a in some embodiments, a porcine large-animal model may be used to test the real-time data capture and analysis solution for all three components of MSPV, $SpO_2$ and PSPs and generate additional normal and ischemic/hypoxic/abnormal PSP data in tissues by reproducing the ischemic experimental model used before. The new data may provide clinically relevant experimental ranges for each component across the entire tissue integrity spectrum, enabling further development and refinement of the matrices.

Figure 14:
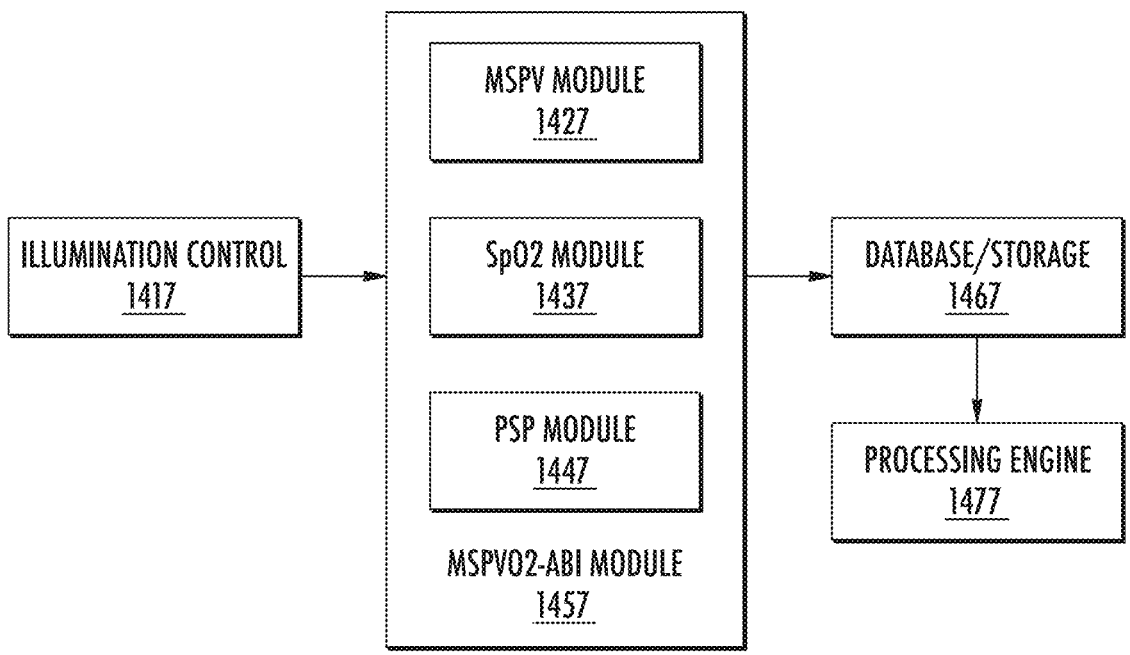
FIG. 14 is a block diagram of an $MSPVO_2$ system in accordance with some embodiments of the present inventive concept.

A $MSPVO_2$-ABI system in accordance with some embodiments of the present inventive concept will be discussed. As illustrated in FIG. 14, the system 1407 includes illumination control 1417; an $MSPVO_2$-ABI module 1457 including an MSPV module 1427, an $SpO_2$ module 1437 and a PSP module 1447; a database/storage module 1467 and a processing engine 1477. It will be understood that although embodiments of the present inventive concept are illustrated in FIG. 14 having a single illumination control, three modules in the $MSPVO_2$-ABI module, a single database and a single processing engine, embodiments of the present inventive concept are not limited to this configuration. There may be more modules or modules may be combined without departing from the scope of the present inventive concept.

The illumination control 1417 in accordance with embodiments discussed herein may include any illumination system suitable for embodiments of the present inventive concept. In some embodiments, the illumination system discussed above with respect to FIG. 1—may be used. In particular, two (2), imaging optical head units (OHU) 1010 may be used that are mounted to flexible attachments 1040 to facilitate easy positioning of each OHU 1010 at the correct focal length for accurate imaging sequence acquisition. In the supine patient at rest, the first OHU may images the palmar surface of the hand and digits 1050; the second OHU 1040 images the ipsilateral posterior tibial or dorsalis pedis region of the foot/ankle 1060. No sphygmomanometers or hand-held dopplers are necessary. The $MSPVO_2$-ABI system 1000 is entirely non-contact and non-invasive. Simultaneous imaging acquisition from both OHUs 1010 captures typically 20-25 seconds of data. It will be understood illumination with two OHUs as discussed herein is discussed as example only and other forms of illumination control may be discussed without departing from the scope of the present inventive concept.

The three modules of the $MSPVO_2$-ABI module 1457 are performed simultaneously. In other words, the imaging sequence performed by the illumination control according to embodiments of the present inventive concept provide an imaging sequence of about 10-12 seconds that provides all the data required for the $MSPVO_2$-ABI module 1457: (1) the real-time blood flow distribution visualization in the entire FOV (MSPV module 1427); (2) the peripheral oxygen saturation at the tissue surface level for the entire FOV ($SpO_2$ module 1437); and (3) the generated PSP data detailing the actual physiology of blood flow distribution in numeric format for analysis (PSP Module 1447). These data are generated in true "real-time" for the entire FOV through parallel (same time) processing of the three individual data streams captured as part of the imaging acquisition.

In particular, the MSPV module 1427 using applies an imaging platform using multi-spectral imaging acquisition and laser speckle contrast analyses to visualize and quantify blood flow distribution—blood flow in vessels and perfusion in tissues—and physiology. MSPV is discussed, for example, in commonly assigned U.S. Pat. Nos. 9,271,658; 9,226,673; and 10,058,256, the contents of which have been incorporated herein by reference as if set forth in their entirety. A comprehensive hardware and software solution, MSPV uses multi-spectral imaging acquisition (multiple wavelength illumination, reflectance capture) and laser spectral contrast analyses. Since dynamic physiology is visualized from time zero (to), image acquisition time may only be 10-20 seconds. The MSPV analysis is executed from the imaging acquisition data in real-time and, thus, the analyzed MSVP video data are presented to the provider in true real-time. By "fusing" anatomic detail with this physiology, the MSPV analysis imaging content has exceptional fidelity. MSPV is non-contact, non-invasive (no dyes or contrast agents), doesn't use ionizing radiation, and is minimal risk to patients or providers even with multiple imaging acquisition episodes.

In parallel to the operations of the MSPV module 1427, the SpO$_2$ module 1437 implements a non-invasive, non-contact determination of peripheral oxygen saturation (SpO$_2$) and local hemoglobin concentration ([Hgb]) in tissues, also in real-time. Embodiments of the present inventive concept discuss an MSPV platform that incorporates SpO$_2$ into the MSPV platform. Since perfusion cannot be inferenced from a relative 'map' of SpO$_2$ distribution, this MSPV-O$_2$ approach is unique in providing real-time perfusion and tissue oxygenation data simultaneously across the entire FOV which is typically 9 cm×9 cm, thus, providing the "02" portion of MSPVO$_2$-ABI. Determination of peripheral Oxygen Saturation is discussed in, for example, commonly assigned U.S. patent application Ser. No. 16/433,716, filed on Jun. 6, 2019, entitled *Determining Peripheral Oxygen Saturation (SpO$_2$) and Hemoglobin Concentration using Multi-Spectral Laser Imaging (MSLI) Methods and Systems*, the contents of which are hereby incorporated herein by reference as if set forth in its entirety.

Finally, in parallel with the other two modules, the PSP Module 1447, is configured to analyze the real-time blood flow distribution (MSPV) metadata to reveal physiologic drivers of that blood flow distribution, Physiologic Status Parameters (PSPs). PSPs may include, for example, tissue perfusion (TP), dynamic change in tissue perfusion (DCTP), tissue ischemia (TI), systolic, diastolic and mean blood pressure (BP), heart rate (HR), and relative index of sympathetic tone. Some embodiments correlate these PSP determinations derived entirely non-invasively with sphygmomanometer measurements of BP and ECG measurement of HR.

The data from each of the modules 1427, 1437 and 1447 may be provided to a database/storage module 1467. This data may be de-identified in compliance with privacy laws. The stored data may be mined at the processing engine 1477 using various techniques of deep machine learning and AI to provide derived data. This derived data may be used to further advance training and diagnosis as discussed herein. Thus, together, the output of the modules 1427, 1437 and 1447 (perfusion, peripheral oxygenation, and cardiovascular hemodynamics) can be used to provide a method of assessing atypical patients with PAD and PVD beyond ABI. Some embodiments provide an entirely new technologic solution, MSPVO$_2$-ABI, in an entirely new form factor that is real-time, accessible, effective and minimally obtrusive in care delivery.

Figure 15:
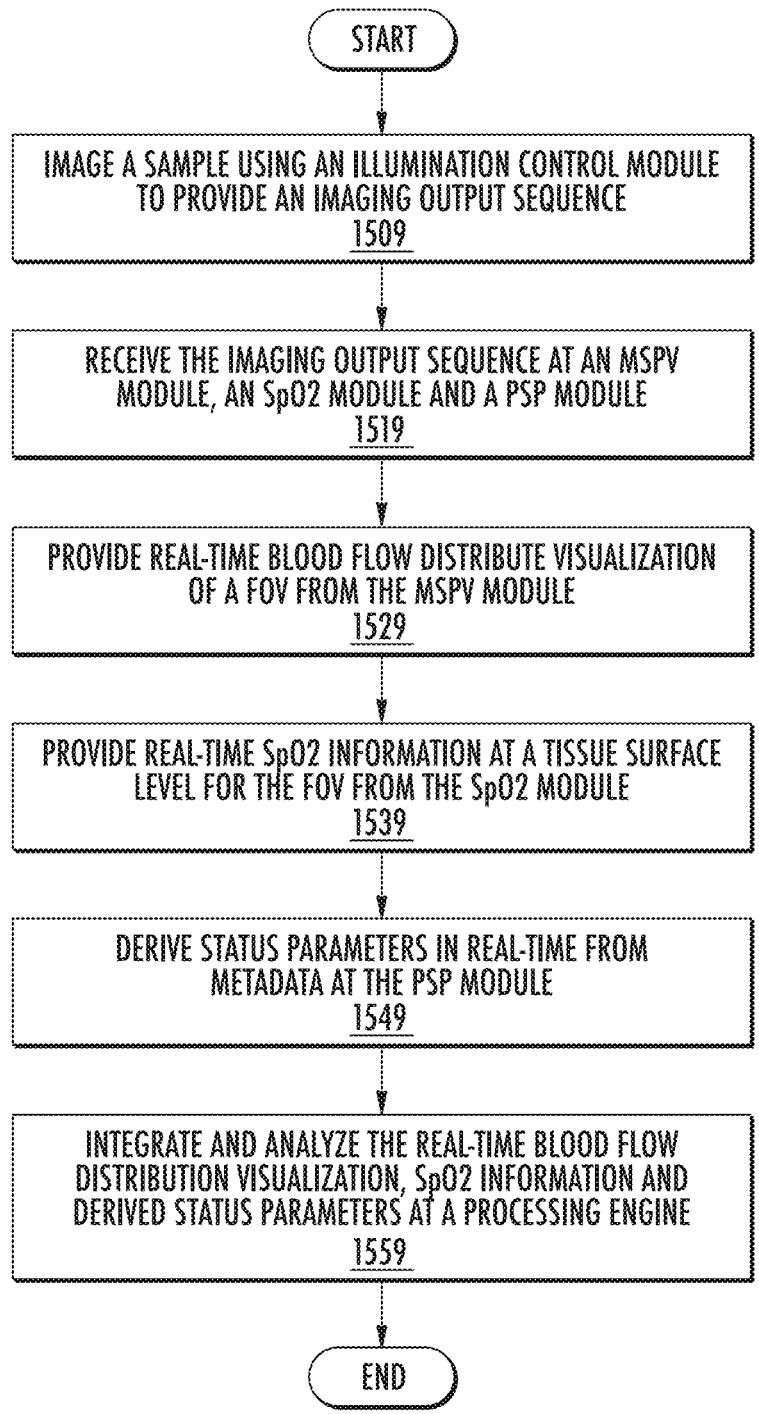
FIG. 15 is a flowchart illustrating various operations in accordance with some embodiments of the present inventive concept.

Referring now to FIG. 15, a flowchart illustrating operations in accordance with various embodiments of the present inventive concept will be discussed. As illustrated in FIG. 15, operations begin at block 1509 by imaging a sample using an illumination control module to provide an imaging output sequence including images and data. As discussed above, in some embodiments, the sample may be imaged using first and second optical head units (OHUs). Each of the first and second OHUs may be configured to a corresponding first and second focal length for a first and second imaging output sequence, respectively. The first OHU may have the first focal length for the imaging output sequence that is configured to illuminate a first portion of sample, for example, a palm of a hand), and provide the first imaging output sequence to the MSVP module, the SpO$_2$ module and the PSP module. The second OHU may have the second focal length for imaging output sequence and may be configured to illuminate a second portion of sample, for example, a foot, different from the first portion, and provide the second imaging output sequence to the MSVP module, the SpO$_2$ module and the PSP module. The OHUs may simultaneously acquiring from about 20 to about 25 seconds of data with the first and second OHUs and provide the acquired data to the MSVP module, the SpO$_2$ module and the PSP module. This data may be analyzing data and displayed in accordance with some embodiments of the preset inventive concept.

Operations continue at block 1519 by receiving the imaging output sequence of the illumination control module simultaneously at a multi-spectral physiologic visualization (MSPV) module, a peripheral oxygen saturation (SpO$_2$) module and a physiologic status parameters (PSP) module. The MSPV module may provide real-time blood flow distribution visualization of a field of view (FOV) responsive to the received imaging output sequence (block 1529). The integrated and analyzed real-time blood flow distribution visualization may be displayed in a form of a video. The SpO$_2$ module may provide real-time SpO$_2$ information at a tissue surface level for the FOV responsive to the received imaging and output sequence (block 1539). The SpO$_2$ information may be displayed in a still image form. The PSP module may derive status parameters in real-time from metadata associated with the received imaging and output sequence of the FOV (block 1549). The status parameters may be displayed in graphic form. The status parameters may include, for example, tissue perfusion (TP), dynamic change in tissue perfusion (DCTP), tissue ischemia (TI), systolic, diastolic and mean blood pressure (BP), heart rate (HR), and/or relative index of sympathetic tone.

The real-time blood flow distribution visualization, SpO$_2$ information and derived status parameters at a processing engine may be integrated and analyzed (block 1559). As discussed herein, the MSVPO2-ABI is not meant to replace cABI but supplement the results thereof. The integrated data output from systems in accordance with embodiments discussed herein may increase the likelihood of early diagnosis. In some embodiments, the data may be processed using artificial intelligence (AI) algorithms and deep learning algorithms.

In some embodiments, the real-time blood flow distribution visualization and the status parameters may be stored in one or more matrix files in a database/storage module. The SpO$_2$ information may be stored as individual value data for each pixel in the FOV and as an averaged per pixel deoxyhemoglobin/oxyhemoglobin ratio for the FOV in the database/storage module.

Figure 16:
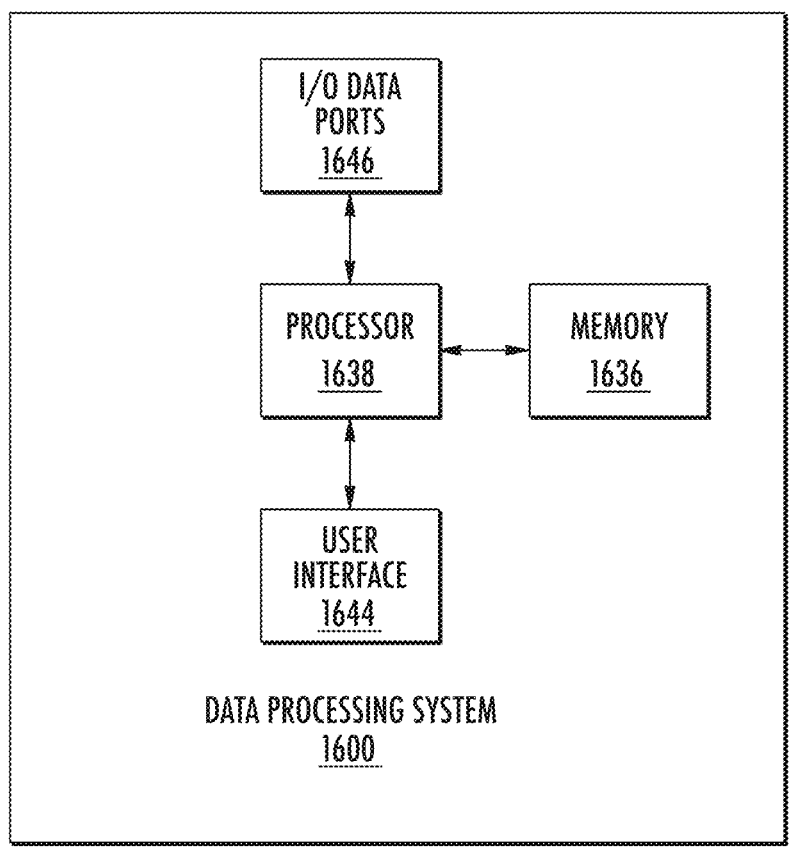
FIG. 16 is a block diagram of a data processing system according to some embodiments of the present inventive concept(s).

Referring now to FIG. 16, a data processing system 1600 that may be used in the systems of, for example, FIG. 14 in any of the modules in accordance with some embodiments of the inventive concept will be discussed. It will be understood that the data processing system 1600 may be included in any of the components of the system without departing from the scope of the present inventive concept. For example, the data processing system 1600 may be included in the processing engine, database/storage module or various elements of the system without departing from the scope of the present inventive concept.

Referring now to FIG. 16, an exemplary embodiment of a data processing system 1600 suitable for use in the systems in accordance with embodiments discussed herein includes a user interface 16644 such as a keyboard, keypad, touchpad or the like, I/O data ports 1646 and a memory 336 that communicates with a processor 1638. The I/O data ports 1646 can be used to transfer information between the data processing system 1600 and another computer system or a network. These components may be conventional components, such as those used in many conventional data processing systems, which may be configured to operate as described herein.

As discussed briefly above, an illumination system generates data streams to obtain three distinct types of data. An imaging sequence of about 10-12 seconds provides data for the MSPVO$_2$-ABI module to provide the real-time blood flow distribution visualization in the entire FOV; the peripheral oxygen saturation at the tissue surface level for the entire FOV; and the generated PSP data detailing the actual physiology of blood flow distribution in numeric format for analysis. This data is generated in true "real-time" for the entire FOV through parallel (same time) processing of the three individual data streams captured as part of the imaging acquisition. The data results are then re-integrated (video for MSPV), still image for SpO$_2$, graphic description of the numeric PSP data) for display. The MSPV data (and metadata-derived PSP data) are captured as a matrix file; the SpO$_2$ data are captured as an individual value for each pixel in the FOV and as the averaged per pixel deoxyhemoglobin/oxyhemoglobin ratio for the entire FOV. This data may be used in combination with cABI to properly identify disease and diagnosis patients in accordance with embodiments discussed herein.

In the drawings and specification, there have been disclosed example embodiments of the inventive concept. Although specific terms are employed, they are used in a generic and descriptive sense only and not for purposes of limitation, the scope of the inventive concept being defined by the following claims.

What is claimed is:

1. A multispectral imaging system comprising:
   an illumination control module that images a sample and provides an imaging output sequence including images and data;
   a multi-spectral physiologic visualization (MSPV) module, a peripheral oxygen saturation (SpO$_2$) module and a physiologic, status parameters (PSP) module that receives the imaging output sequence of the illumination control module simultaneously,
   wherein the MSPV module provides real-time blood flow distribution visualization of a field of view (FOV) responsive to the received imaging output sequence;
   wherein the SpO$_2$ module is integrated within the multi-spectral imaging system and provides real time SpO$_2$ information at a tissue surface level for the FOV responsive to the received imaging and output sequence; and
   wherein the PSP module derives status parameters in real-time from metadata associated with the received imaging and output sequence of the FOV; and
   a processing engine integrates and analyzes the real-time blood flow distribution visualization, SpO$_2$ information and derived status parameters.

2. The system of claim 1, further comprising a user interface that displays the integrated and analyzed real-time blood flow distribution visualization, SpO$_2$ information and derived status parameters,
   wherein the MSPV module provides the blood flow and distribution data in form of a video;
   wherein the SpO$_2$ module provides the SpO$_2$ information in a still image form; and
   wherein the PSP module provides the status parameters in graphic form.

3. The system of claim 1, further comprising database/storage module,
   wherein the MSPV module and the PSP module store the real-time blood flow distribution visualization and the status parameters in one or more matrix files in the database/storage module; and
   wherein the integrated SpO$_2$ module stores the SpO$_2$ information as individual value data for each pixel in the FOV and as an averaged per pixel deoxyhemoglobin/oxyhemoglobin ratio for the FOV in the database/storage module.

4. The system of claim 3, wherein the processing engine processes data stored in the database/storage module using artificial intelligence (AI) algorithms and deep learning algorithms.

5. The system of claim 3, wherein data stored in the database/storage module is de-identified having no identifiers in digital datasets.

6. The system of claim 1, wherein the imaging output sequence is an imaging output sequence of from about 10 to about 12 seconds.

7. The system of claim 1, wherein the status parameters comprise one or more of tissue perfusion (TP), dynamic change in tissue perfusion (DCTP), tissue ischemia (TI), systolic, diastolic and, mean blood pressure (BP), heart rate (HR), and relative index of sympathetic tone.

8. The system of claim 1, wherein the illumination control comprises first and second optical head units (OHUs), each of the first and second OHUs having a corresponding first and second focal length fbr a first d second imaging output sequence, respectively,
   wherein the first OHU having the first focal length for the imaging output sequence illuminates a first portion of the sample and provide the first imaging output sequence to the MSVP module, the SpO$_2$ module and the PSP module; and
   wherein the second OHU having the second focal length for the imaging output sequence illuminates a second portion of the sample, different from the first portion, and provide the second imaging output sequence to the MSVP module, the SpO$_2$ module and the PSP module.

9. The system of claim 8, wherein the first and second OHUs are coupled to first and second flexible attachments such that first and second OHUs may be positioned at the first and second portions of the sample, respectively.

10. The system of claim 8:
    wherein the first and second OHUs simultaneously acquire from about 20 to about 25 seconds of data and provide the acquired data to the MSVP module, the SpO$_2$ module and the PSP module; and
    wherein the processing engine analyzes data from the MSVP module, the SpO$_2$ module and the PSP module; and,
    wherein the system farther comprises a physical display, the physical display displaying results from the processing engine in real-time.

11. The system of claim 8, wherein the illumination control is positioned on a mobile cart and wherein the mobile cart is repositioned to obtain image sequences from other portions of the sample different from the first and second portions.

12. A method for imaging a sample using a multispectral imaging system, the method comprising:

imaging a sample using an illumination control module to provide an imaging output sequence including images and data;

receiving the imaging output sequence of the illumination control module simultaneously at a multi-spectral physiologic visualization (MSPV) module, an integrated peripheral oxygen saturation ($SpO_2$) module and a physiologic status parameters (PSP) module;

providing, from the MSPV module, real-time blood flow distribution visualization of a field of view (FOV) responsive to the received imaging output sequence;

providing, from the integrated $SpO_2$ module, real-time $SpO_2$ information at a tissue surface level for the FOV responsive to the received imaging and output sequence; and deriving, at the PSP module, status parameters M real-time from metadata associated with the received imaging and output sequence of the FOV; and integrating and analyzing the real-time blood flow distribution visualization $SpO_2$ information and derived status parameters at a processing engine.

13. The method of claim 12, further comprising:
displaying the integrated and analyzed real-time blood flow distribution visualization in a form of a video;
displaying the $SpO_2$ information in a still image form; and
displaying the status parameters in graphic form.

14. The method of claim 12, further comprising:
storing the real-time blood flow distribution visualization and the status parameters in one or more matrix files in a database/storage module; and
storing the $SpO_2$ information as individual value data for each pixel in the FOV and as an averaged per pixel deoxyhemoglobin/oxyhemoglobin ratio for the FOV in the database/storage module.

15. The method of claim 14, wherein the processing further comprises processing data stored in the database/storage module using artificial intelligence (AI) algorithms and deep learning algorithms.

16. The method of claim 14, wherein, storing data in the database/storage module comprising storing de-identified data having no identifiers in digital datasets.

17. The method of claim 12, wherein the status parameters comprise one or more of tissue perfusion (TP), dynamic change in tissue perfusion (DCTP), tissue ischemia (TI), systolic, diastolic and mean blood pressure (BP), heart rate (HR), and relative index of sympathetic tone.

18. The method of claim 12, wherein imaging a sample comprises:
imaging the sample using first and second optical head units (OHUs), each of the first and second OHUs corresponding to first and second focal length for a first and second imaging output sequence, respectively,
wherein the first OHU having the first focal length for the imaging output sequence illuminates a first portion of the sample and provides the first imaging output sequence to the MSVP module, the $SpO_2$ module and the PSP module; and
wherein the second OHU having the second focal length for the imaging output sequence illuminates a second portion of the sample, different from the first portion, and provide the second imaging, output sequence to the MSVP module, the $SpO_2$, module and the PSP module.

19. The method of claim 18, wherein the first and second OHUs are coupled to first and second flexible attachments such that first and second OHUs may be positioned at the first and second portions of the sample, respectively.

20. The method of claim 18, farther comprising:
simultaneously acquiring from about 20 to about 25 seconds of data with the first and second OHUs and providing the acquired data to the MSVP module, the $SpO_2$ module and the PSP module; and
analyzing data from the MSVP module, the $SpO_2$ module and the PSP module; and
displaying results from the processing engine in real-time.

* * * * *

UNITED STATES PATENT AND TRADEMARK OFFICE
CERTIFICATE OF CORRECTION

PATENT NO. : 10,948,350 B2
APPLICATION NO. : 16/560335
DATED : March 16, 2021
INVENTOR(S) : Ferguson, Jr. et al.

It is certified that error appears in the above-identified patent and that said Letters Patent is hereby corrected as shown below:

In the Specification

Column 9, Line 42: Please correct "blood flow distribution" to read -- *blood flow distribution* --
Lines 43-44: Please correct "and physiology" to read -- *and physiology* --

Column 10, Line 3: Please correct "MSPVO$_2$-ABI" to read -- MSPVO$_2$-ABI --
Line 25: Please correct "MSPVO$_2$-ABI" to read -- MSPVO$_2$-ABI --

Column 18, Line 4: Please correct "(ξ1) and CIM (ξ2)" to read -- (ζ1) and CIM (ζ2) --
Line 5: Please correct "–Δ≤ξ1–ξ2+Δ," to read -- –Δ≤ζ1 – ζ2+Δ, --
Line 7: Please correct "ξ1 – ξ2 falls within the Α equivalence" to read -- ζ1 – ζ2 falls within the Δ equivalence --

Column 21, Line 5: Please correct "hypoxemia 4 hypoxia" to read -- hypoxemia → hypoxia --

Column 22, Line 57: Please correct "blood flow distribution" to read -- *blood flow distribution* --
Lines 58: Please correct "and physiology" to read -- *and physiology* --

In the Claims

Column 26, Claim 3, Line 3: Please correct "further comprising database/" to read -- further comprising a database/ --
Claim 8, Line 34: Please correct "focal length fbr a first d second" to read -- focal length for a first and second --

Column 27, Claim 12, Line 16: Please correct "parameters M" to read -- parameters in --

Column 28, Claim 18, Line 24: Please correct "second imaging, output" to read -- second imaging output --

Signed and Sealed this
Eleventh Day of May, 2021

Drew Hirshfeld
*Performing the Functions and Duties of the
Under Secretary of Commerce for Intellectual Property and
Director of the United States Patent and Trademark Office*